(12) United States Patent
Kim et al.

(10) Patent No.: US 9,999,611 B2
(45) Date of Patent: Jun. 19, 2018

(54) SIRT 1 ACTIVATOR INCLUDING SYRINGARESINOL

(71) Applicant: AMOREPACIFIC CORPORATION, Seoul (KR)

(72) Inventors: Byung Gyu Kim, Yongin-si (KR); Hyun Woo Jeong, Yongin-si (KR); Su Kyung Kim, Yongin-si (KR); Si Young Cho, Yongin-si (KR); Chan Woong Park, Yongin-si (KR); Dae Bang Seo, Yongin-si (KR); Wan Gi Kim, Yongin-si (KR); Sang Jun Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days. days.

(21) Appl. No.: 15/160,197

(22) Filed: May 20, 2016

(65) Prior Publication Data

US 2016/0263077 A1    Sep. 15, 2016

Related U.S. Application Data

(62) Division of application No. 14/352,444, filed as application No. PCT/KR2012/008556 on Oct. 18, 2012, now Pat. No. 9,913,823.

(30) Foreign Application Priority Data

| Oct. 18, 2011 | (KR) | 10-2011-0106561 |
| Oct. 24, 2011 | (KR) | 10-2011-0108904 |
| Oct. 24, 2011 | (KR) | 10-2011-0108914 |
| Oct. 26, 2011 | (KR) | 10-2011-0109961 |

(51) Int. Cl.

| A61K 31/34 | (2006.01) |
| A23L 2/52 | (2006.01) |
| A61K 36/258 | (2006.01) |
| A23L 33/11 | (2016.01) |
| A23L 33/105 | (2016.01) |

(52) U.S. Cl.
CPC ............. *A61K 31/34* (2013.01); *A23L 2/52* (2013.01); *A23L 33/105* (2016.08); *A23L 33/11* (2016.08); *A61K 36/258* (2013.01); *A23V 2002/00* (2013.01)

(58) Field of Classification Search
None
See application file for complete search history.

(56) References Cited

U.S. PATENT DOCUMENTS

| 5,922,760 A * | 7/1999 | Akimoto | A61K 31/34 |
| | | | 514/458 |
| 6,525,081 B1 | 2/2003 | Matsumoto et al. | |
| 6,814,958 B1 | 11/2004 | Sekimoto | |
| 2002/0156129 A1 | 10/2002 | Kuraishi et al. | |
| 2011/0091584 A1 | 4/2011 | Kajiya et al. | |
| 2012/0238515 A1* | 9/2012 | Pan | A61K 31/35 |
| | | | 514/27 |
| 2013/0090377 A1 | 4/2013 | Jeon et al. | |

FOREIGN PATENT DOCUMENTS

| EP | 1072254 A1 | 1/2001 |
| JP | 1987292785 | 12/1987 |
| JP | 11302142 A | 11/1999 |
| JP | H11310530 A | 11/1999 |
| JP | 2000290198 A | 10/2000 |
| JP | 200229953 A | 1/2002 |
| JP | 2002241308 A | 8/2002 |
| JP | 2005350483 A | 12/2005 |
| JP | 2007302644 A | 11/2007 |
| JP | 2009263359 | 11/2009 |
| KR | 1020030087728 A | 11/2003 |
| KR | 1020040033983 A | 4/2004 |
| KR | 1020050022944 A | 3/2005 |
| KR | 1020080010030 A | 1/2008 |
| KR | 1020080019837 A | 3/2008 |
| KR | 1020090108208 A | 10/2009 |
| KR | 1020110050772 A | 5/2011 |
| KR | 1020110063573 A | 6/2011 |
| KR | 1020110110053 A | 10/2011 |
| WO | 9921844 A1 | 5/1999 |
| WO | 2009154237 | 12/2009 |
| WO | 2010037127 A1 | 4/2010 |

OTHER PUBLICATIONS

COPD Symptoms Website www.medicinenet.com/copd_chronic_obstructive_pulmonary_disease/article.htm, accessed Aug. 14, 2017).*

(Continued)

*Primary Examiner* — Kortney L. Klinkel
*Assistant Examiner* — William Y Lee
(74) *Attorney, Agent, or Firm* — Cantor Colburn LLP

(57) ABSTRACT

The present invention relates to a compound of Formula 1, and an SIRT 1 activator including, as an active ingredient, derivatives thereof or pharmaceutically acceptable salts thereof. The present invention also relates to a composition including the SIRT 1 activator for detoxification, for the improvement of metabolic disorders, for the prevention or improvement of eye diseases, or the prevention or improvement of immune diseases.

7 Claims, 21 Drawing Sheets

(56) References Cited

OTHER PUBLICATIONS

Nakagawa et al. Hiroshima Journal of Medical Sciences (1985), 34(3), 303-9 (Year: 1985).*
District of Columbia Tobacco Free Coalition, What's in Cigarette Smoke Website, at web address: www.dctfc.org/whats-in-cigarette-smoke/, accessed Mar. 12, 2018. (Year: 2018).*
Annika I. Smeds, et al., "Quantification of a Broad Spectrum of Lignans in Cereals, Oilseeds, and Nuts", J. Agric. Food Chem., vol. 55, No. 4, (2007), pp. 1337-1346.
Japanese Office Action—Japanese Application No. 2014-536990 dated Aug. 2, 2016.
Japanese Office Action No. JP 2014-536990 dated Dec. 6, 2010 with Brief English Translation.
T. Yamazaki, et al., "(+)-Syringaresinol-di-O—B-D-glucoside, a phenolic compound from Acanthopanax senticosus Harms, suppresses proinflammatory mediators in SW982 human synovial sarcoma cells by inhibiting activating protein-1 and/or nuclear factor-kB activites", Toxicology in Vitro 21 (2007), pp. 1530-1537.
3rd Party Submission for U.S. Appl. No. 14/352,444 dated Dec. 6, 2015.
International Search Report with English Translation for International Application No. PCT/KR2012/008556 dated Feb. 25, 2013.
Khobrakova et al., Immunomodulating Properties of Lignan Glucoside From Cultivated Cells of Scorzonera Hispanica L., Pharmaceutical Chemistry Journal Jul. 2003, vol. 37, Issue 7, pp. 345-346.
NFOA, dated Jul. 31, 2015, KCL0197US.
Nishibe, S., Bioactive Phenolic Compounds for Cancer Prevention from Herbal Medicine, Food Factors for Cancer Prevention 1997, pp. 276-279.
Written Opinion for International Application No. PCT/KR2012/008556 dated Feb. 25, 2013.
Japanese Office Action with English Translation of 2nd Office Action for Application No. 2016-213317 dated Oct. 18, 2017.
Tsukumo, et al., "Involvement of nitric oxide in itch-scratch response of NC mice", Folia Pharmacol. Jpn., 1999, vol. 114, Suppl. 1, pp. 17-21. (Abstract and Brief English traslation of OA).
Wang, et al., Lignans from the Roots of Wikstroemia indica and Their DPPH Radical Scavenging and Nitric Oxide Inhibitory Activities, Chem. Pharm. Bull. vol. 53 (No. 10) pp. 1348-1351 (2005).

* cited by examiner

SIRT 1 ACTIVATOR INCLUDING SYRINGARESINOL

CROSS-REFERENCE TO RELATED APPLICATIONS

This application is a divisional of U.S. patent application Ser. No. 14/352,444, filed on Apr. 17, 2014, which claims priority to PCT Application No. PCT/KR2012/008556, filed on Oct. 18, 2012, which claims priority to Korean Patent Application No. 10-2011-0106561, filed on Oct. 18, 2011, Korean Patent Application No. 0-2011-0108904, filed on Oct. 24, 2011, Korean Patent Application No. 0-2011-0108914, filed on Oct. 24, 2011, and Korean Patent Application No. 10-2011-0109961, filed on Oct. 26, 2011, and all the benefits accruing therefrom under 35 U.S.C. § 119, the contents of which in their entirety are herein incorporated by reference.

TECHNICAL FIELD

The present disclosure relates to an SIRT1 activating agent containing a compound of Chemical Formula 1, a derivative thereof or a pharmaceutically acceptable salt thereof as an active ingredient. The present disclosure also relates to a composition for detoxification, improvement of metabolic disorder, prevention or improvement of eye disease or prevention or improvement of immune disease containing the SIRT1 activating agent.

BACKGROUND ART

Smoking is known as an important risk factor of many diseases which are the leading causes of human death. The major disease caused by smoking include lung cancer, chronic obstructive pulmonary disease (COPD), coronary artery disease, cerebrovascular disease such as stroke, heart failure, circulatory disease, laryngopharyngeal cancer, oral cancer, etc.

Cigarette smoke contains over 4,000 toxic substances, including carcinogens. Among them, tar which is a mixture of several toxic substances and nicotine are known as important harmful ingredients. Since the harmful ingredients contained in tobacco suppress SIRT1 which is known as human longevity gene, they render cigarette smokers vulnerable to inflammations or severe diseases such as chronic obstructive pulmonary disease (COPD). Also, smoking is known to cause abnormality in mitochondrial function.

Owing to the change in lifestyles with industrial development and surplus high-calorie food, humankind is exposed to the risk of metabolic diseases represented by obesity, type 2 diabetes, hyperlipidemia, fatty liver, etc. Considering that, among them, obesity is the major cause of metabolic diseases such as type 2 diabetes, hyperlipidemia and fatty liver, the other metabolic diseases could be prevented by preventing or improving obesity.

Obesity is most commonly caused by energy input exceeding consumption of energy by the body. Specifically, surplus energy is stored in adipose tissue in the form of triglyceride. Although the adipose tissue can store a large amount of surplus energy as if a rubber balloon, the size of adipocytes is increased at the same time. In addition, if the amount of surplus energy to be stored exceeds the capacity of the adipose tissue, lipid dysregulation lipotoxicity occur in which energy is stored in other tissues such as muscle, liver, etc. The fat stored in each tissue is changed into free fatty acid through lipolysis. The free fatty acid is known to inhibit insulin signaling through signaling mechanisms involving JNK, PKC, etc. The inhibition of insulin signaling necessarily induces insulin resistance and, as a result, leads to various metabolic diseases such as hyperglycemia, hyperlipidemia, hypercholesterolemia, type 2 diabetes, fatty liver, etc. As such, obesity is a severe problem since it is not just an appearance concern but is accompanied by various adult diseases.

The retina is an organ considered part of the central nervous system. Fully grown retinal cells do not normally divide like most neurons existing in the brain. Therefore, if the function of the retinal cells is degenerated, disorder can occur easily in tissue or organ level when compared with other system and, as a result, aging proceeds fast. Oxidative stress is a major cause of the degeneration of the retinal cell function because the retina, optic nerve, photoreceptor cells and lens constituting eyes are consistently exposed to the cause of oxidative damage such as light and UV. Upon oxidative damage, mitochondrial DNA in intraocular cells is damaged. Since mitochondria lack enzymes that can repair the damaged DNA, the damaged mitochondrial DNA is accumulated in the cells with time. If the mitochondrial DNA becomes unstable, modification occurs in mitochondria protein synthesized therefrom. As a result, the mitochondrial membrane potential decreases, followed by decreased production of mitochondrial energy (ATP) and relatively increased generation of reactive oxygen species. Consequently, modification occurs in the DNA, protein and lipid constituting the cells and aging of eyes or eye disease such as macular degeneration, uveitis, glaucoma, diabetic retinopathy and cataract occurs. Accordingly, eye disease can be prevented or improved by inhibiting destabilization of mitochondrial DNA. However, the most widely known method of delaying eye aging at present is an indirect method of using antioxidant to reduce oxidative stress.

When the human body is invaded by viruses, bacteria, etc., the infected cells produce histamine, kinin, etc., which dilate capillaries of the damaged part and thus allow various immune cells including macrophages and killer cells to easily reach the wound site. After the immune cells such as macrophages engulf the invading viruses, bacteria, etc., various enzymes in lysosomes break them down and the immune response is terminated.

Immune response is an essential for maintenance of the body's homeostasis along with energy metabolism. Innate immunity is a primary defense mechanism against nonspecific sources of infection from outside and defends our bodies from incessant invasion from outside through inflammatory responses. The inflammatory responses are strictly regulated because they have a great impact on cells and tissues. If the inflammatory response is not controlled normally, various immune diseases such as hay fever, rheumatoid arthritis, allergy, atopic dermatitis, etc. can occur. Moreover, since chronic inflammation wherein the expression of inflammation-related genes is increased even in the absence of external pathogens can cause metabolic diseases such as type 2 diabetes by affecting insulin resistance, the regulation of immune response is a prerequisite for the control of homeostasis of individuals.

DISCLOSURE

Technical Problem

The present disclosure is directed to providing an SIRT1 activating agent which activates SIRT1.

The present disclosure is also directed to providing a composition having excellent detoxifying effect.

The present disclosure is also directed to providing a composition having excellent effect of preventing or improving metabolic disorder, specifically having effect of preventing or improving metabolic disorder by regulating fat metabolism.

The present disclosure is also directed to providing a composition having excellent effect of preventing or improving eye disease, specifically having effect of preventing or improving age-related eye disease by increasing sirtuin 1 (SIRT1) expression and mitochondrial synthesis in retinal cells.

The present disclosure is also directed to providing a composition having excellent effect of preventing or improving immune disease, specifically having effect of preventing or improving immune disease by promoting SIRT1 expression in immune cells and differentiation into type 2 immune cells.

Technical Solution

In an aspect, the present disclosure provides an SIRT1 activating agent containing a compound of Chemical Formula 1, a derivative thereof or a pharmaceutically acceptable salt thereof as an active ingredient:

[Chemical Formula 1]

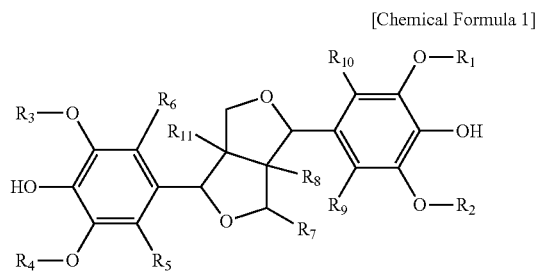

wherein $R_1$, $R_2$, $R_3$ or $R_4$ is independently an unbranched or branched $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group, and $R_5$, $R_6$, $R_7$, $R_8$, $R_9$, $R_{10}$ or $R_{11}$ is independently hydrogen or an unbranched or branched $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group.

In another aspect, the present disclosure provides a composition for detoxification containing the SIRT1 activating agent.

In another aspect, the present disclosure provides a composition for preventing or improving metabolic disorder containing the SIRT1 activating agent.

In another aspect, the present disclosure provides a composition for preventing or improving eye disease containing the SIRT1 activating agent.

In another aspect, the present disclosure provides a composition for preventing or improving immune disease containing the SIRT1 activating agent.

Advantageous Effects

A sirtuin 1 (SIRT1) activating agent according to the present disclosure increases SIRT1 expression and enhances SIRT1 activity.

A composition according to the present disclosure has superior detoxifying effect, particularly superior effect of detoxifying smoking-induced toxicity by promoting SIRT1 activity and cellular activity that have been decreased due to smoking.

The composition according to the present disclosure has excellent effect of preventing or improving metabolic disorder, specifically obesity, type 2 diabetes, hyperlipidemia or fatty liver, by increasing SIRT1 expression, inhibiting fatty acid synthesis and promoting fatty acid oxidation at the same time, and increasing PGC-1 expression.

Also, the composition according to the present disclosure has excellent effect of preventing or improving eye disease, specifically age-related eye disease, by promoting SIRT1 expression, enhancing mitochondrial biosynthesis and restoring mitochondrial function in retinal cells.

The composition according to the present disclosure can enhance immunity by promoting SIRT1 expression and inhibiting inflammatory response in immune cells and converting and immune cells to type 2 immune cells and particularly has excellent effect of preventing or improving immune disease such as allergy, atopic dermatitis, hay fever or rheumatoid arthritis.

BEST MODE FOR CARRYING OUT INVENTION

Figure 1:
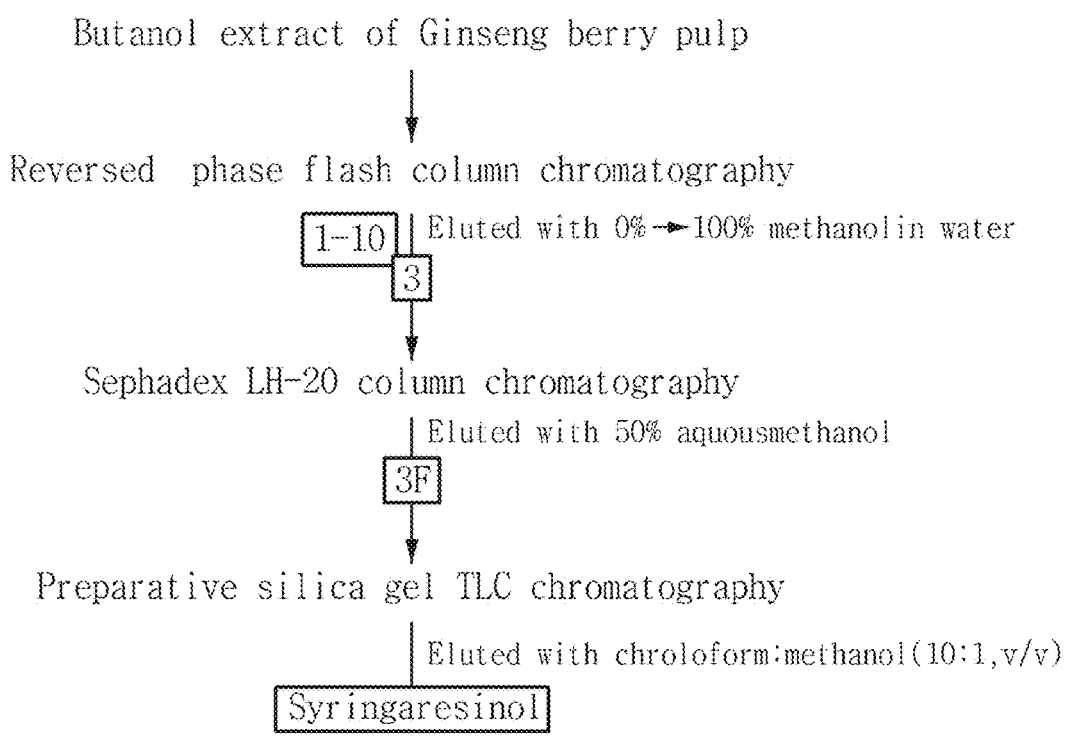
FIG. 1 schematically describes a method of isolating and purifying syringaresinol from a ginseng berry extract.

In the present disclosure, the term "extract" is used as a broad concept and refers to any substance extracted from a natural product, regardless of extraction method, extraction solvent, extracted ingredients or the type of extract.

As used herein, the term "derivative" refers to any compound having substituent(s) at substitutable position(s) of the corresponding compound. The substituent is not particularly limited. For example, the substituent may independently be a $C_{1-10}$ acyclic hydrocarbon group which may be substituted with hydroxyl, phenoxy, thienyl, furyl, pyridyl, cyclohexyl, alkylalcohol, alkyldialcohol or substituted phenyl; a $C_{5-6}$ cyclic hydrocarbon group which may be substituted with hydroxyl, hydroxymethyl, methyl or amino; or a sugar residue, although not being limited thereto. As used herein, the term "sugar residue" refers to the group available on elimination of one hydrogen atom from a carbohydrate molecule. As such, it may mean, for example, a residue derived from a monosaccharide or an oligosaccharide.

As used herein, the term "pharmaceutically acceptable" means being devoid of substantial toxic effects when used with a usual medicinal dosage and thereby being approvable or approved by a regulatory agency of the government or being listed in the US Pharmacopoeia or other generally recognized pharmacopoeia for use in animals, more particularly in human.

As used herein, the term "pharmaceutically acceptable salt" refers to a salt of the compound of the present disclosure which is pharmaceutically acceptable and possesses the desired pharmacological activity of the parent compound. The salt may include: (1) an acid addition salt formed with an inorganic acid such as hydrochloric acid, hydrobromic acid, sulfuric acid, nitric acid, phosphoric acid, etc. or formed with an organic acid such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, ethane-1,2-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid; or (2) a salt formed when an acidic proton present in the parent compound is replaced. In addition to the pharmaceutically acceptable salt, the compound according to the present disclosure may include any salt, hydrate or solvate that can be prepared according to commonly employed methods.

Hereinafter, the present disclosure is described in detail.

In an aspect, the present disclosure provides an SIRT1 activating agent containing a compound of Chemical Formula 1, a derivative thereof or a pharmaceutically acceptable salt thereof as an active ingredient:

[Chemical Formula 1]

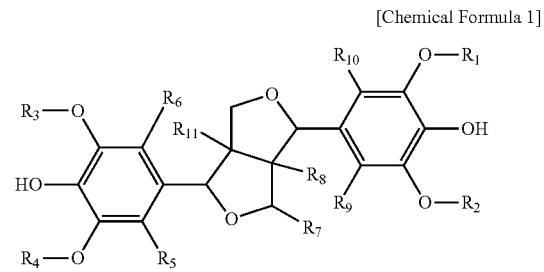

wherein $R_1$, $R_2$, $R_3$ or $R_4$ is independently an unbranched or branched $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group, and $R_5$, $R_6$, $R_7$, $R_8$, $R_9$, $R_{10}$ or $R_{11}$ is independently hydrogen or an unbranched or branched $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group.

In an exemplary embodiment of the present disclosure, the compound may be syringaresinol.

As used herein, the term "syringaresinol" refers to a lignan-based compound having a chemical structure represented by Chemical Formula 2. It may be synthesized chemically or extracted from one or more of flax seed, phellodendri cortex, acanthopanacis cortex, sesame seed and ginseng berry. The flax seed, phellodendri cortex, acanthopanacis cortex and sesame seed respectively include all parts of the plant, for example, leaves, stem, root, fruit or seed and the ginseng berry includes the rind or pulp of ginseng berry.

[Chemical Formula 2]

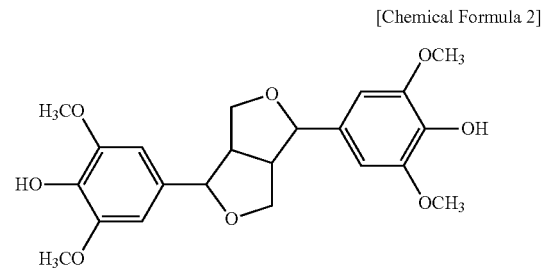 [SMILES: COc1cc(C2OCC3C(c4cc(OC)c(O)c(OC)c4)OCC23)cc(OC)c1O]

In the present disclosure, the "syringaresinol" may be obtained by extracting one or more of flax seed, phellodendri cortex, acanthopanacis cortex, sesame seed and ginseng berry with water, an organic solvent or a mixture of water and an organic solvent. The organic solvent includes one or more selected from a group consisting of alcohol, acetone, ether, ethyl acetate, diethyl ether, methyl ethyl ketone and chloroform, although not being limited thereto. The alcohol includes a $C_1$-$C_5$ lower alcohol and the $C_1$-$C_5$ lower alcohol includes one or more selected from a group consisting of methanol, ethanol, isopropyl alcohol, n-propyl alcohol, n-butanol and isobutanol, although not being limited thereto.

The SIRT1 activating agent according to the present disclosure may contain 0.0001-10 wt % of the active ingredient based on the total weight of the activating agent. However, the content of the active ingredient may be greater or smaller than the above range as long as SIRT1 activating effect is achieved and toxicity does not occur. The above-described range is appropriate not only to derive the effect desired by the present disclosure and satisfy both the stability and safety of the composition but also in terms of cost effectiveness. Specifically, if the content of the compound of Chemical Formula 1, specifically syringaresinol, is less than 0.0001 wt %, SIRT1 may not be activated. And, if it exceeds 10 wt %, the safety and stability of the SIRT1 activating agent may be unsatisfactory. More specifically, the active ingredient of the present disclosure may be contained in an amount of 0.0005-8 wt %, 0.001-6 wt % or 0.01-4 wt %.

The syringaresinol may be contained in an extract of flax seed, phellodendri cortex, acanthopanacis cortex, sesame seed or ginseng berry.

In an exemplary embodiment of the present disclosure, syringaresinol may be isolated and purified from ginseng berry by a procedure including: preparing an alcohol extract of ginseng berry pulp; eluting the prepared alcohol extract with a solvent including one or more of water and alcohol and obtaining fractions thereof; and performing chromatography, specifically thin-layer chromatography (TLC), on the obtained fractions using an organic solvent as an eluent. The organic solvent may include one or more selected from a group consisting of alcohol, acetone, ether, ethyl acetate, diethyl ether, methyl ethyl ketone and chloroform, and the alcohol may include a $C_1$-$C_5$ alcohol. In an exemplary embodiment of the present disclosure, the composition may contain the syringaresinol purified as described above as an active ingredient.

In another aspect, the present disclosure provides composition for detoxification containing the SIRT1 activating agent.

As used herein, the term "detoxification" refers to removal of the action of a toxic substance included in the body.

The SIRT1 activating agent can detoxify a toxic substance included in the body, and specifically can detoxify smoking-induced toxicity.

Sirtuin 1 (SIRT1), which is one of deacetylases, deacetylates PGC-1α by physically interacting with PGC-1α at several lysine sites, thereby activating PGC-1α. The activated PGC-1α promotes mitochondrial biosynthesis and removes cytotoxic substances such as reactive oxygen species by reacting with transcription factors. Accordingly, it is expected to that smoking-induced toxicity can be detoxified by restoring SIRT1 activity that has been decreased due to smoking. The compound of Chemical Formula 1, specifically syringaresinol, can detoxify smoking-induced toxicity by promoting SIRT1 activity and cellular activity that have been decreased due to smoking. Accordingly, the composition containing the compound of Chemical Formula 1, specifically syringaresinol, may have detoxifying effect.

In an exemplary embodiment of the present disclosure, the syringaresinol may be contained in the composition as an extract of flax seed, phellodendri cortex, acanthopanacis cortex, sesame seed or ginseng berry. Specifically, it may be contained in a fraction which is particularly effective for detoxification.

The composition for detoxification according to the present disclosure may contain 0.001-20 wt %, specifically 0.01-10 wt %, more specifically 0.1-5 wt % of the SIRT1 activating agent based on the total weight of the composition. This range is appropriate not only to derive the effect desired by the present disclosure and satisfy both the stability and safety of the composition but also in terms of cost effectiveness. Specifically, if the content of the SIRT1 activating agent is less than 0.01 wt %, sufficient skin detoxifying effect may not be achieved. And, if it exceeds 20 wt %, the safety and stability of the composition may be unsatisfactory.

In another aspect, the present disclosure provides a composition for preventing or improving metabolic disorder, containing the SIRT1 activating agent.

If fat metabolism can be regulated, obesity may be prevented and improved since excessive fat accumulation can be prevented. One of the methods for preventing excessive fat accumulation is to control diet, i.e. calorie restriction. Through calorie restriction, body weight can be decreased and metabolic disease can be improved by lowering blood lipid concentration. It is known that calorie restriction leads to increased SIRT1 expression and a similar phenomenon occurs as in calorie restriction when the activation of SIRT1 is induced. SIRT1 is an NAD$^+$-dependent histone deacetylase which regulates energy metabolism such as glucose synthesis, fatty acid oxidation, etc. Accordingly, a substance which promotes the expression of SIRT1 is expected to be capable of regulating fat metabolism and preventing or improving metabolic disorder such as obesity, type 2 diabetes, hyperlipidemia and fatty liver.

To sustain life, living organisms intake nutrients and digest, absorb and store them as a source of energy. Also, they carry out various biological activities using energy released therefrom. This phenomenon is called "metabolism".

As used herein, the term "metabolic disorder" refers to a condition in which a living organism including human or an animal cannot normally carry out metabolic activities and includes carbohydrate metabolic disorder or lipid metabolic disorder. The carbohydrate metabolic disorder or the lipid metabolic disorder includes symptoms or diseases caused by disorder of carbohydrate or lipid metabolism, specifically symptoms or diseases caused by excessive fat accumulation induced by disorder of fatty acid metabolism. Examples may include obesity, type 2 diabetes, hyperlipidemia or fatty liver.

Syringaresinol can suppress fat accumulation in the body by increasing SIRT1 expression, inhibiting fatty acid synthesis and promoting fatty acid oxidation. This can be confirmed by the fact that syringaresinol suppresses the expression of fatty acid synthesis-related genes such as ADD1/SREBP1c, ACC and FAS, promotes the expression of fatty acid oxidation-related genes such as ACO, CPT1 and mCAD and enhances fatty acid oxidation. Also, syringaresinol can enhance consumption of body fat and suppress accumulation of surplus fat by promoting energy metabolism, specifically fat metabolism. This can be confirmed by the fact that syringaresinol increases the expression of peroxisome proliferator-activated receptor coactivator 1 (PGC-1) which regulates the expression of energy metabolism-related genes. Accordingly, the composition containing syringaresinol may prevent or improve metabolic disorder such as obesity, type 2 diabetes, hyperlipidemia or fatty liver, which his caused by carbohydrate or lipid metabolic disorder.

In an exemplary embodiment of the present disclosure, the syringaresinol may be contained in the composition as an extract of flax seed, phellodendri cortex, acanthopanacis cortex, sesame seed or ginseng berry. Specifically, it may be contained in a fraction which is particularly effective for improving metabolic disorder.

The composition according to the present disclosure may contain 0.001-20 wt %, specifically 0.01-10 wt %, more specifically 0.1-5 wt % of the SIRT1 activating agent based on the total weight of the composition. This range is appropriate not only to derive the effect desired by the present disclosure and satisfy both the stability and safety of the composition but also in terms of cost effectiveness. Specifically, if the content of the SIRT1 activating agent is less than 0.01 wt %, sufficient effect of improving metabolic disorder may not be achieved. And, if it exceeds 20 wt %, the safety and stability of the composition may be unsatisfactory.

In another aspect, the present disclosure provides a composition for preventing or improving eye disease, containing the SIRT1 activating agent.

SIRT1, which is an $NAD^+$-dependent histone deacetylase, is known to restore mitochondrial function and thus prevent cellular aging by increasing mitochondrial biosynthesis in muscle, etc., and thereby increasing the proportion of mitochondria having stable DNAs in cells. In particular, it is known that a transgenic mouse model of retinal degeneration exhibits expression of SIRT1 at abnormal locations in retinal cells such as retinal ganglion cells, intraretina cells, photoreceptor cells and retinal pigment epithelial cells and also exhibits accelerated cell death. Accordingly, a substance that increases SIRT1 expression will be able to prevent and improve eye disease, particularly age-related eye disease, by promoting mitochondrial biosynthesis and restoring mitochondrial function in retinal cells and reducing instability of mitochondrial DNA, thereby reducing cell damage and death.

The compound of Chemical Formula 1, specifically syringaresinol, can induce increased energy production and decrease of reactive oxygen species by increasing SIRT1 expression in aged retinal cells to a level comparable to that of young retinal cells, promoting mitochondrial synthesis in retinal cells and recovering mitochondrial function. Accordingly, the composition containing the compound of Chemical Formula 1, specifically syringaresinol, as an active ingredient can prevent or improve eye disease by preventing or improving the aging of retinal cells.

As used herein, the term "eye disease" refers to a disease related with eyes and includes the disease of eyeball. And, as used herein, the term "age-related eye disease" includes not only the eye disease caused by the decline in biological function with age but also the eye disease exhibiting symptoms similar to those occurring in the elderly whose biological function is degenerated as compared to young people. In an exemplary embodiment of the present disclosure, the eye disease includes one caused by the disorder of mitochondrial function in retinal cells or oxidative stress. In another exemplary embodiment of the present disclosure, the eye disease includes age-related eye disease and includes macular degeneration including age-related macular degeneration, uveitis, glaucoma, diabetic retinopathy or cataract, but is not limited thereto.

In another exemplary embodiment of the present disclosure, the syringaresinol may be contained in the composition as an extract of flax seed, phellodendri cortex, acanthopanacis cortex, sesame seed or ginseng berry. Specifically, it may be contained in a fraction which is particularly effective for prevention or improvement of eye disease.

The composition according to the present disclosure may contain 0.001-20 wt %, specifically 0.01-10 wt %, more specifically 0.1-5 wt % of the SIRT1 activating agent based on the total weight of the composition. This range is appropriate not only to derive the effect desired by the present disclosure and satisfy both the stability and safety of the composition but also in terms of cost effectiveness. Specifically, if the content of the SIRT1 activating agent is less than 0.01 wt %, sufficient effect of improving eye disease may not be achieved. And, if it exceeds 20 wt %, the safety and stability of the composition may be unsatisfactory.

In another aspect, the present disclosure provides a composition for preventing or improving immune disease, containing the SIRT1 activating agent.

Immune cells can be largely divided into type 1 immune cells which defend against pathogens by inducing pro-inflammatory responses and type 2 immune cells which inhibit anti-inflammatory responses and help tissue reconstruction. It is known that the number of type 1 immune cells is greatly increased in chronic inflammation and the chronic inflammation state can be relieved by inducing differentiation of the type 1 immune cells into type 2 immune cells. This suggests that immune disease such as allergy, atopic dermatitis, hay fever, rheumatoid arthritis, etc. can be prevented and treated by controlling the type of immune cells.

It is known that activation of SIRT1 which is an $NAD^+$-dependent histone deacetylase that regulates various cellular responses including energy metabolism, cell cycle, DNA restoration, etc. leads to suppression of chronic inflammation. Accordingly, a substance that promotes SIRT1 expression will be able to improve immune disease by suppressing inflammatory response.

The compound of Chemical Formula 1, specifically syringaresinol, promotes SIRT1 expression in peripheral blood mononuclear cells (PBMCs) including immune cells such as B cells, T cells, macrophages, dendritic cells, NK cells, etc., suppresses inflammatory response as one of innate immune responses and inhibits the production of reactive oxygen species which are signaling mediators and also products of inflammatory response. Also, since the compound of Chemical Formula 1, specifically syringaresinol, promotes the expression of transcriptional regulators necessary for inducement of differentiation into type 2 immune cells, such as PGC-1α and PGC-1β, and increases the expression of the genes that are mainly expressed in type 2 immune cells, such as IL-10 and arginase I, the compound of Chemical Formula 1, specifically syringaresinol, can promote the conversion of immune cells to type 2 immune cells. Accordingly, the composition containing the compound of Chemical Formula 1, specifically syringaresinol, as an active ingredient can enhance immunity and can prevent or improve immune disease, particularly chronic immune disease.

In an exemplary embodiment of the present disclosure, the immune disease refers to a disease related with a defensive mechanism against external pathogens that may harm the body and means a disease exhibiting various immune responses such as antigen-antibody reaction, vasodilation, fever and inflammatory response. In another exemplary embodiment of the present disclosure, the immune disease includes one or more of allergy, atopic dermatitis, hay fever and rheumatoid arthritis, but is not limited thereto.

In another exemplary embodiment of the present disclosure, the syringaresinol may be contained in the composition as an extract of flax seed, phellodendri cortex, acanthopanacis cortex, sesame seed or ginseng berry. Specifically, it may be contained in a fraction which is particularly effective for prevention or improvement of immune disease.

The composition according to the present disclosure may contain 0.001-20 wt %, specifically 0.01-10 wt %, more specifically 0.1-5 wt % of the SIRT1 activating agent based on the total weight of the composition. This range is appropriate not only to derive the effect desired by the present disclosure and satisfy both the stability and safety of the composition but also in terms of cost effectiveness. Specifically, if the content of the SIRT1 activating agent is less than 0.01 wt %, sufficient effect of preventing or improving immune disease may not be achieved. And, if it exceeds 20 wt %, the safety and stability of the composition may be unsatisfactory.

In an exemplary embodiment of the present disclosure, the composition for detoxification, preventing or improving metabolic disorder, preventing or improving eye disease or preventing or improving immune disease may be a composition for oral administration.

In another exemplary embodiment of the present disclosure, the composition for detoxification, preventing or improving metabolic disorder, preventing or improving eye disease or preventing or improving immune disease may be a food composition. The food composition includes an indulgence food or health food composition.

The composition may prevent or improve metabolic disorder such as obesity, type 2 diabetes, hyperlipidemia or fatty liver.

The food composition may prevent or improve eye disease such as macular degeneration, uveitis, glaucoma, diabetic retinopathy or cataract.

The food composition may prevent or improve immune disease such as allergy, atopic dermatitis, hay fever or rheumatoid arthritis.

The formulation of the food composition is not particularly limited. For example, it may be formulated into tablet, granule, powder, liquid such as drink, caramel, gel, bar, etc. Those skilled in the art may select and add the ingredients commonly used in the art to each formulation of the food composition without difficulty. In this case, a synergic effect may be achieved.

Determination of the dosage of the active ingredient is in the level of those skilled in the art. A daily dosage may be, for example, 0.1-5000 mg/kg/day, more specifically 50-500 mg/kg/day. However, the dosage may vary depending on various factors including the age and physical condition of a subject, the presence or absence of complication(s), or the like, without being limited thereto.

In another exemplary embodiment of the present disclosure, the composition for detoxification, preventing or improving metabolic disorder, preventing or improving eye disease or preventing or improving immune disease may be a pharmaceutical composition.

The pharmaceutical composition may exhibit detoxifying effect and specifically may detoxify smoking-induced toxicity.

The pharmaceutical composition may prevent or improve metabolic disorder and specifically may prevent or improve obesity, type 2 diabetes, hyperlipidemia or fatty liver.

The pharmaceutical composition may prevent or treat eye disease and specifically may prevent or treat macular degeneration, uveitis, glaucoma, diabetic retinopathy or cataract.

The pharmaceutical composition may enhance immunity and may prevent or treat immune disease. Specifically, it may prevent or treat allergy, atopic dermatitis, hay fever or rheumatoid arthritis.

In an exemplary embodiment of the present disclosure, the pharmaceutical composition may be administered orally or parenterally, e.g., rectally, topically, transdermally, intravenously, intramuscularly, intraperitoneally, subcutaneously, etc.

A formulation for oral administration may be tablet, pill, soft or hard capsule, granule, powder, fine granule, liquid, emulsion or pellet, although not being limited thereto. These formulations may further contain, in addition to the active ingredient, a diluent (e.g., lactose, dextrose, sucrose, mannitol, sorbitol, cellulose or glycine), a lubricant (e.g., silica, talc, stearic acid or polyethylene glycol) or a binder (e.g., magnesium aluminum silicate, starch paste, gelatin, tragacanth, methyl cellulose, sodium carboxymethyl cellulose or polyvinylpyrrolidone). In some cases, they may further contain a pharmaceutical additive such as a disintegrant, an absorbent, a colorant, a flavoring agent, a sweetener, etc. The tablet may be prepared according to the common mixing, granulation or coating method.

A formulation for parenteral administration may be injection, drop, lotion, ointment, gel, cream, suspension, emulsion, suppository, patch or spray, although not being limited thereto.

The dosage of the active ingredient of the pharmaceutical composition according to the present disclosure will vary depending on the age, sex and body weight of a subject, particular pathological condition and severity thereof, administration route or the discretion of a diagnoser. Determination of the dosage considering these factors is in the level of those skilled in the art. A daily dosage may be, for example, 0.1-100 mg/kg/day, more specifically 5-50 mg/kg/day, although not being limited thereto.

In another exemplary embodiment of the present disclosure, the composition for detoxification, preventing or improving metabolic disorder, preventing or improving eye disease or preventing or improving immune disease may be a cosmetic composition.

The cosmetic composition may exhibit detoxifying effect and specifically may detoxify smoking-induced toxicity.

The cosmetic composition may prevent or improve metabolic disorder and specifically may prevent or improve obesity, type 2 diabetes, hyperlipidemia or fatty liver.

The cosmetic composition may enhance immunity and may prevent or treat immune disease. Specifically, it may prevent or treat allergy, atopic dermatitis, hay fever or rheumatoid arthritis.

The cosmetic composition according to the present disclosure may be provided in the form of any formulation suitable for topical application. For example, it may be provided in the form of solution, oil-in-water emulsion, water-in-oil emulsion, suspension, solid, gel, powder, paste, foam or aerosol. These formulations may be prepared according to methods commonly employed in the art.

The cosmetic composition according to the present disclosure may further contain a humectant, an emollient, a surfactant, a UV absorbent, a preservative, a sterilizer, an antioxidant, a pH adjusting agent an organic or inorganic pigment, a fragrance, a cooling agent or a deodorant. The amount of these ingredients may be determined easily by those skilled in the art within a range not negatively affecting the purpose and effect of the present disclosure. They may be added in an amount of 0.01-5 wt %, specifically 0.01-3 wt %, based on the total weight of the composition.

MODE FOR INVENTION

Hereinafter, the present disclosure will be described in detail through an example and test examples. However, the following example and test examples are for illustrative purposes only and it will be apparent to those of ordinary skill in the art that the scope of the present disclosure is not limited by the example and test examples.

[Example] Isolation and Analysis of Syringaresinol

1. Pretreatment of Ginseng Berry

Live ginseng berry was harvested. After removing the seed and rind of the ginseng berry, only the pulp was dried under sunlight or using hot air to obtain dried ginseng berry pulp.

2. Isolation of Syringaresinol from Ginseng Berry Pulp Extract and Analysis Thereof 3 L of water or alcohol was added to 1 kg of the dried ginseng berry pulp. After extracting at room temperature or under reflux, followed by filtering and concentration at 40-45° C. under reduced pressure, 300 g of a ginseng berry pulp extract was obtained. The extract was treated with ether to remove oil-soluble components and then crude saponin was extracted with butanol and concentrated. Then, syringaresinol was isolated and purified therefrom as follows. First, 194 g of the sample was purified by reversed-phase (ODS) column chromatography. As the eluent, 100% water was used in the beginning. Subsequently, methanol was increased gradually by 10% and, finally, 100% methanol was used as the eluent. As a result, fractions GB-1 through GB-10 were obtained. Among the fractions, the fraction GB-3 which exhibits SIRT1 expression activity was concentrated and subjected to Sephadex LH-20 column chromatography using 50% aqueous methanol. Among the resulting fractions, the fraction GB-3-6 exhibiting SIRT1 expression activity was concentrated and subjected to preparative silica gel TLC using chloroform:methanol (10:1) as an eluent. As a result, an active fraction with an $R_f$ value of 0.67 was purified. This procedure is schematically described in FIG. 1.

Through NMR spectroscopic analysis and database search, the isolated and purified active compound was identified as syringaresinol. Mass analysis was conducted to confirm this. As a result of ESI-mass analysis in the positive mode, $[M+Na]^+$ (m/z=440.9) and $[2M+Na]^+$ (m/z=858.9) peaks were observed and the molecular weight was calculated as 418. And, the result of NMR spectroscopic analysis was as in Chemical Formula 3. Accordingly, the isolated and purified active compound was confirmed to be syringaresinol.

[Chemical Formula 3]

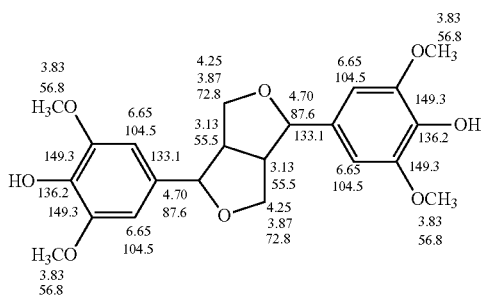

As such, syringaresinol was isolated from the ginseng berry pulp.

[Test Example 1] Evaluation of SIRT1 Expression Recovering Effect in Gingival Fibroblasts Experiment was conducted to evaluate whether syringaresinol can recover SIRT1 expression that has been decreased due to smoking in gingival fibroblasts.

1. Culturing of Gingival Fibroblasts

Gingival fibroblasts were obtained from tissue biopsies of patients having healthy gingiva. The tissue biopsy was put in a 15-mL test tube holding Dulbecco's modified Eagle's medium (DMEM, Gibco Co., USA) and blood and impurities were removed by washing 3 times. Then, the tissue biopsy was transferred onto a 100-mm tissue culture dish holding DMEM containing 10% fetal bovine serum (Gibco Co., USA) and 1% antibiotics (penicillin G 10,000 units/mL, amphotericin B 25 μg/mL, Gibco Co., USA) and finely cut to 1 $mm^2$ using a No. 15 blade. Then, 5-6 pieces were uniformly distributed on a 60-mm culture dish. After incubation for about 30 minutes in a 5% $CO_2$ incubator at 37° C. and 100% humidity such that the tissue was uniformly attached on the bottom of the culture dish, 3 mL of DMEM containing 10% fetal bovine serum and 1% antibiotics was added. The culture medium was exchanged with 2-3 day intervals until a single layer of cells was formed. Then, after removing the culture medium and washing 2 times, the cells attached to the culture dish were separated using 0.25% trypsin/EDTA (1×, Gibco Co., USA) and transferred to a 100-mm tissue culture dish. The culture medium was exchanged with 2-3 day intervals until sufficient cell proliferation was achieved and subculturing was performed 5-6 times at a ratio of 1:3-4.

2. Preparation of Cigarette Smoke Condensate (CSC)

An automatic smoking machine (Heinr Borgwaldt RM 20, Germany) was used to burn 40 3R4F cigarettes under the ISO smoking condition (puff volume: 35 mL, puff duration: 2 seconds, puff frequency: 1 minute, butt length: tip paper+3 mm) and cigarette smoke condensate was collected using the Cambridge glass fiber filter. The collected cigarette smoke condensate was extracted in dichloromethane by sonicating for 30 minutes and then concentrated. The concentrated cigarette smoke condensate was dissolved again in dimethyl sulfoxide (DMSO) to a final concentration of 100 mg/mL, filtered using a 0.22-μm syringe filter and kept at −70° C. until use.

3. PCR

The gingival fibroblasts subcultured 5-6 times were seeded onto a 24-well plate, with 1×10⁴ cells per well. After culturing for 1 day, the cigarette smoke condensate was added with a concentration of 100 μg/mL and the syringaresinol obtained in Example was added after dissolving in DMSO to a concentration of 50 or 100 μg/mL. A control group was treated with DMSO corresponding to 1/1000 of the volume of the culture medium. Also, a group which was treated with neither the cigarette smoke condensate nor the test substance was prepared. After culturing for 2 days, the cells were washed 2 times with cold PBS and RNA was extracted therefrom using the TRIzol reagent (Invitrogen). Then, cDNA was synthesized from the extracted RNA (1 μg/μL) using a reverse transcription system (Promega). The expression pattern of the SIRT1 and GAPDH genes was monitored using the synthesized cDNA and predesigned primers and probes (Applied Biosystems; SIRT1, Hs01009006_m1; GAPDH, Hs99999905_m1). PCR reaction and analysis were carried out using the Rotor-Gene 3000 system (Corbett Research, Sydney, Australia). The result is shown in FIG. 2.

Figure 2:
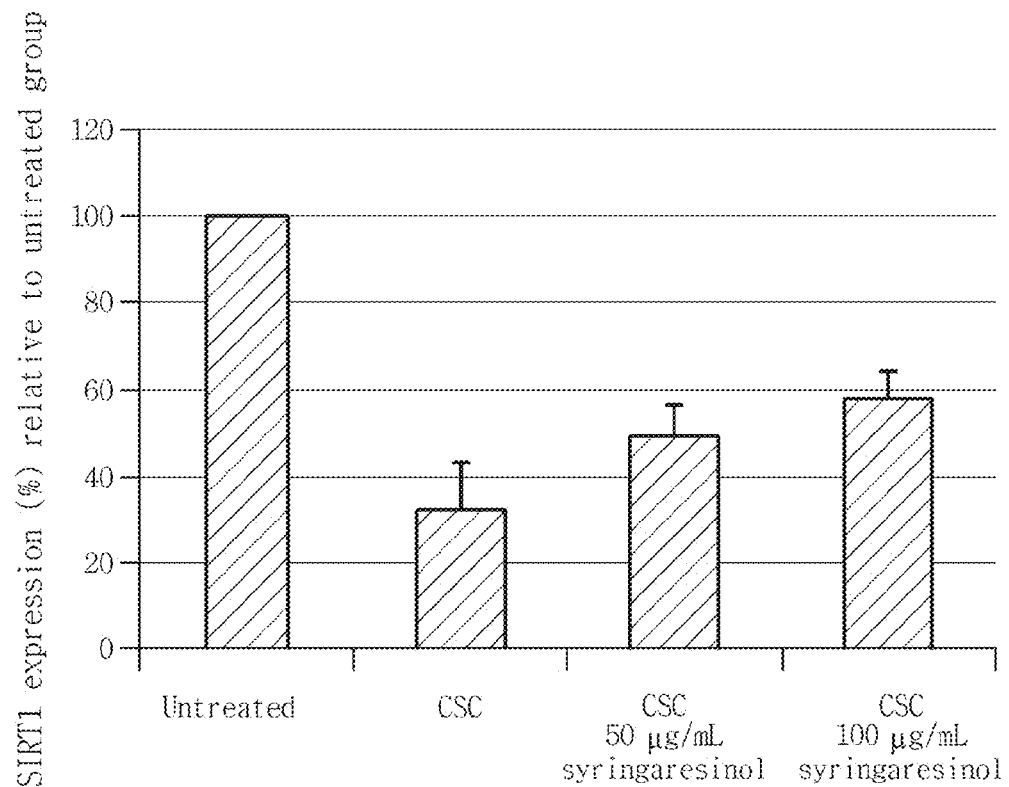
FIG. 2 shows the SIRT1 expression promoting effect of syringaresinol.

As can be seen from FIG. 2, syringaresinol increased SIRT1 expression in gingival fibroblasts, which had been decreased due to smoking, in a concentration-dependent manner. Accordingly, it can be seen that syringaresinol can detoxify smoking-induced toxicity by increasing SIRT1 expression.

[Test Example 2] Evaluation of Cellular Activity Promoting Effect in Gingival Fibroblasts (MTT Assay)

Gingival fibroblasts subcultured for 5-6 times in substantially the same manner as in Test Example 1 were seeded onto a 24-well plate, with $1\times10^4$ cells per well. After culturing for 1 day, cigarette smoke condensate was added with a concentration of 100 μg/mL in substantially the same manner as in Test Example 1 and the syringaresinol obtained in Example was added after dissolving in DMSO to a concentration of 50 or 100 μg/mL. A control group was treated with DMSO corresponding to 1/1000 of the volume of the culture medium. Also, a group which was treated with neither the cigarette smoke condensate nor the test substance was prepared. After culturing for 2 days and adding 300 μL of 3-(4,5-dimethylthiazol-2-yl)-2,5-diphenyltetrazolium bromide (MTT; Sigma, USA) dissolved in physiological saline per each well, the cells were cultured for 4 hours. After removing the culture medium and dissolving formazan crystals by adding 200 μL of dimethyl sulfoxide (DMSO; Junsei, Japan), absorbance was measured at 540 nm using an ELISA reader (Spectra MAX 250, Molecular Devices Co., USA). Each experiment was repeated 3 times. The result is shown in FIG. 3.

Figure 3:
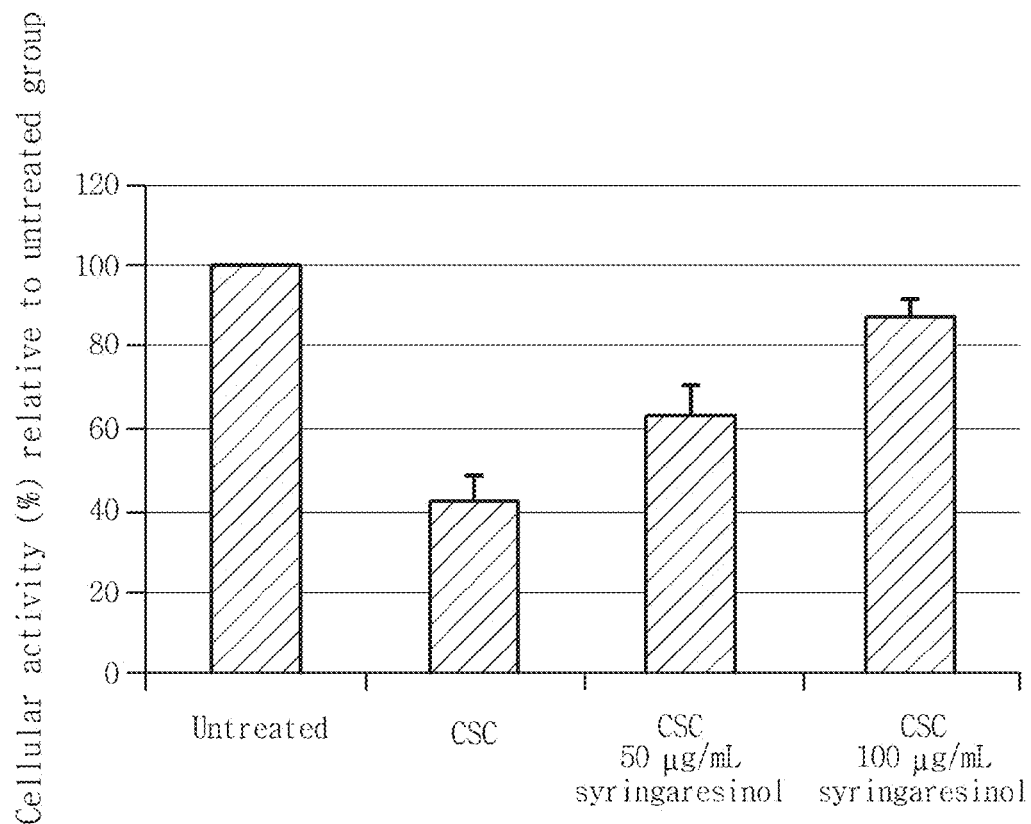
FIG. 3 shows the cellular activity promoting effect of syringaresinol.

As can be seen from FIG. 3, syringaresinol recovered cellular activity, which had been decreased due to smoking, to a level substantially comparable to the normal level. Accordingly, it can be seen that syringaresinol can detoxify smoking-induced toxicity by recovering cellular activity which has declined due to smoking.

[Test Example 3] Evaluation of SIRT1 Expression Promoting Effect in Adipocytes, Hepatocytes and Myocytes The SIRT1 gene expression promoting effect of syringaresinol in human adipocytes, hepatocytes and myocytes was evaluated as follows.

Human adipocytes, hepatocytes and myocytes were purchased from Zen-Bio (Research Triangle Park, N.C., USA) and cultured in a 5% $CO_2$ incubator using respectively an adipocyte medium (OM-AM, Zen-Bio), a hepatocyte medium (HM-2, Zen-Bio) and a myocyte medium (SKM-D, SKM-M, Zen-Bio). The cells were treated with syringaresinol dissolved in DMSO to a concentration of 20, 50 or 100 μM for 24 hours. A negative control group was treated with DMSO corresponding to 1/1000 of the volume of the culture medium.

The cells treated with each sample were washed 2 times with cold PBS and RNA was extracted therefrom using the TRIzol reagent (Invitrogen). Then, cDNA was synthesized from the extracted RNA (5 mg) using a reverse transcription system (Fermentas, Glen Burnie, Md., USA). The expression pattern of the SIRT1 and GAPDH genes was monitored by qRT-PCR using the synthesized cDNA and predesigned primers and probes. PCR reaction and analysis were carried out using the Rotor-Gene 3000 system (Corbett Research, Sydney, Australia). The result is shown in FIG. 4.

Figure 4:
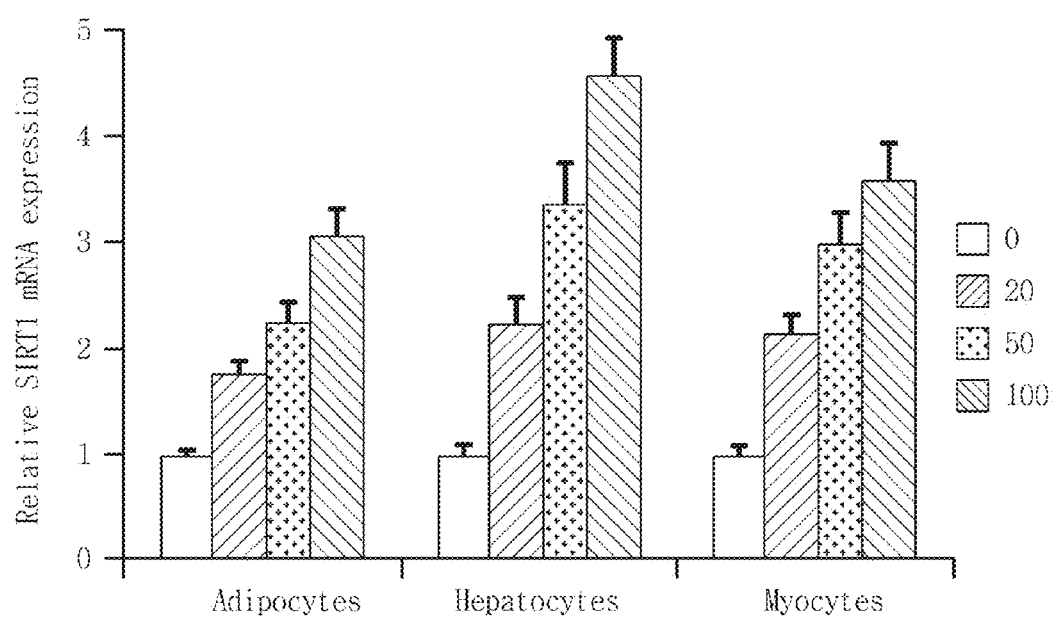
FIG. 4 shows the change in expression of the SIRT1 gene in human adipocytes, hepatocytes and myocytes treated with 20, 50 and 100 μM syringaresinol.

As can be seen from FIG. 4, syringaresinol increased SIRT1 expression in human adipocytes, hepatocytes and myocytes in a concentration-dependent manner. Accordingly, it can be seen that syringaresinol can improve metabolic disorder, specifically lipid metabolic disorder.

[Test Example 4] Evaluation of Ability to Regulate Expression of Fat Metabolism-Related Genes in Adipocytes and Hepatocytes Human adipocytes, hepatocytes and myocytes were treated with 50 μM syringaresinol and washed with PBS in substantially the same manner as in Test Example 3. RNA was extracted from the cells and cDNA was synthesized therefrom. The change in expression pattern of fatty acid synthesis-related genes such as ADD1/SREBP1c, ACC, FAS, etc. and fatty acid oxidation-related genes such as ACO, CPT1, mCAD, etc. was measured by qRT-PCR. The result of comparing with a control group which was treated only with DMSO is shown in FIGS. 5-10.

Figure 5:
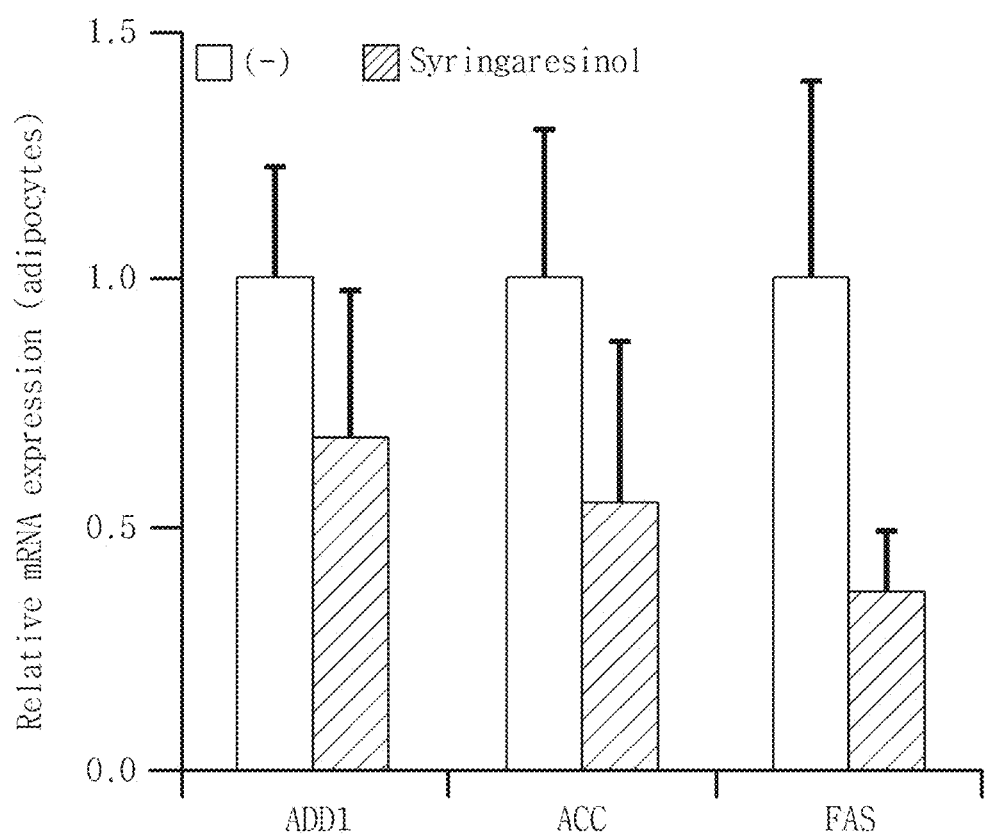
FIG. 5 shows the decrease in expression of fatty acid synthesis-related genes in human adipocytes treated with 50 μM syringaresinol.
Figure 6:
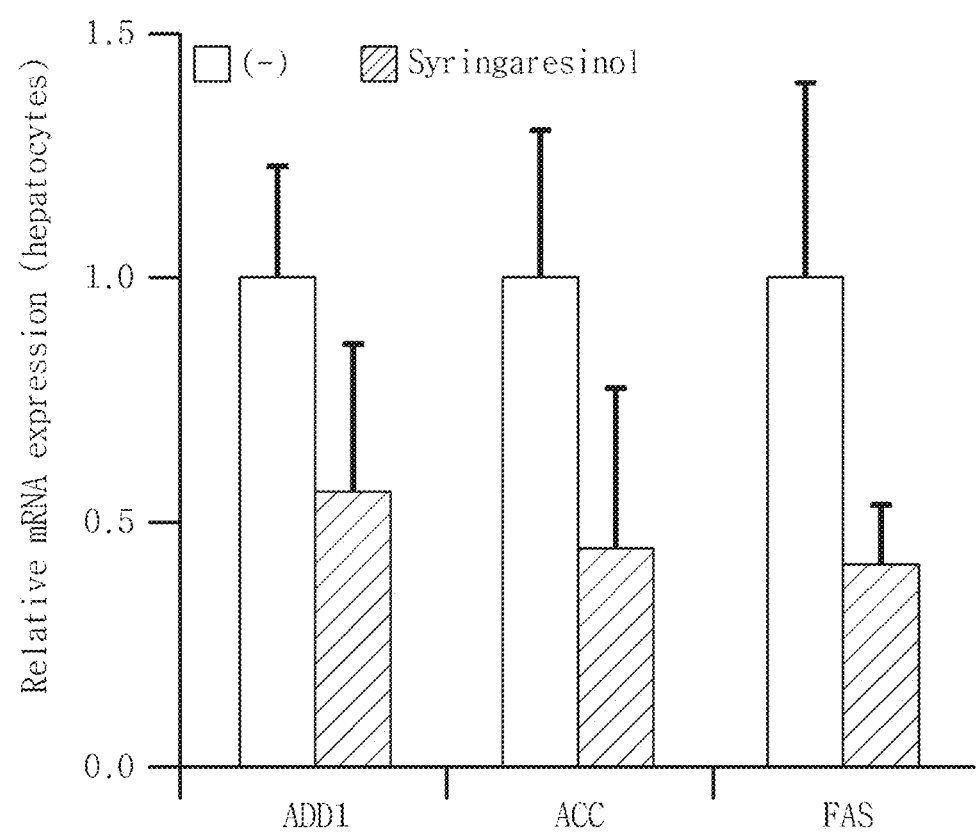
FIG. 6 shows the decrease in expression of fatty acid synthesis-related genes in human hepatocytes treated with 50 μM syringaresinol.
Figure 7:
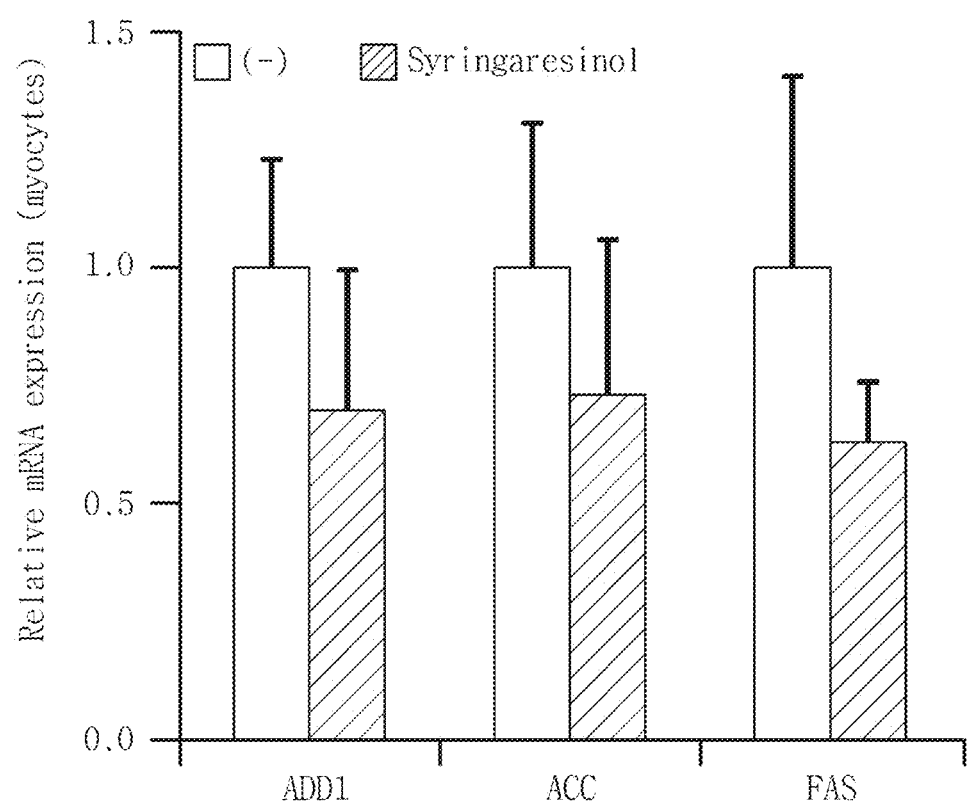
FIG. 7 shows the decrease in expression of synthesis-related genes in human myocytes treated with 50 μM syringaresinol.
Figure 8:
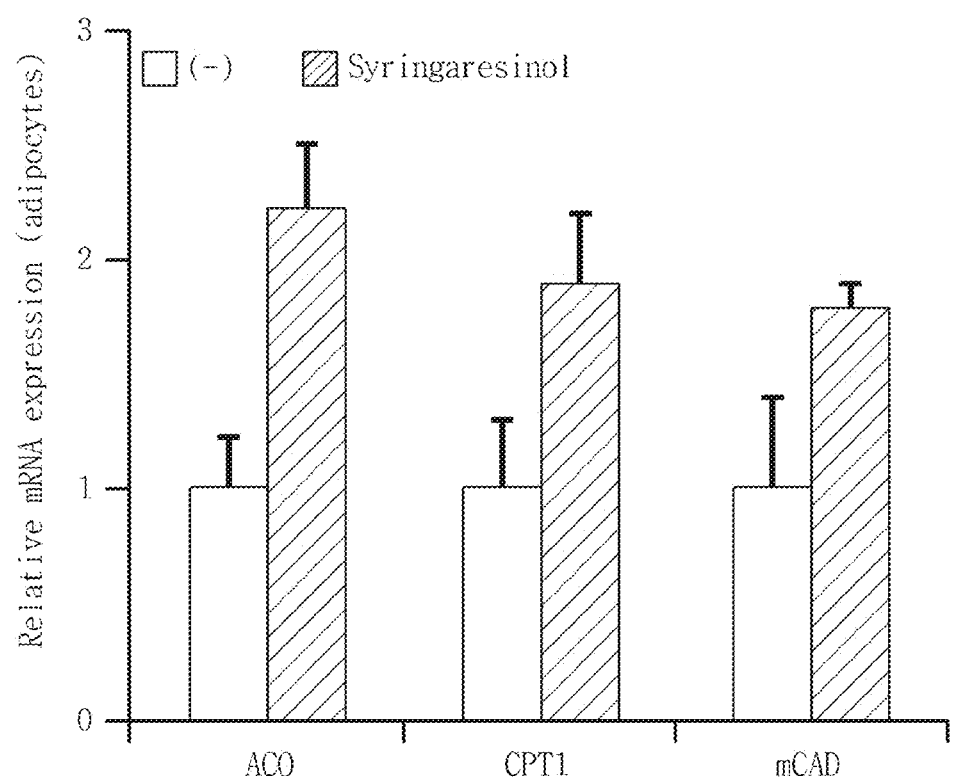
FIG. 8 shows the increase in expression of fatty acid oxidation-related genes in human adipocytes treated with 50 μM syringaresinol.
Figure 9:
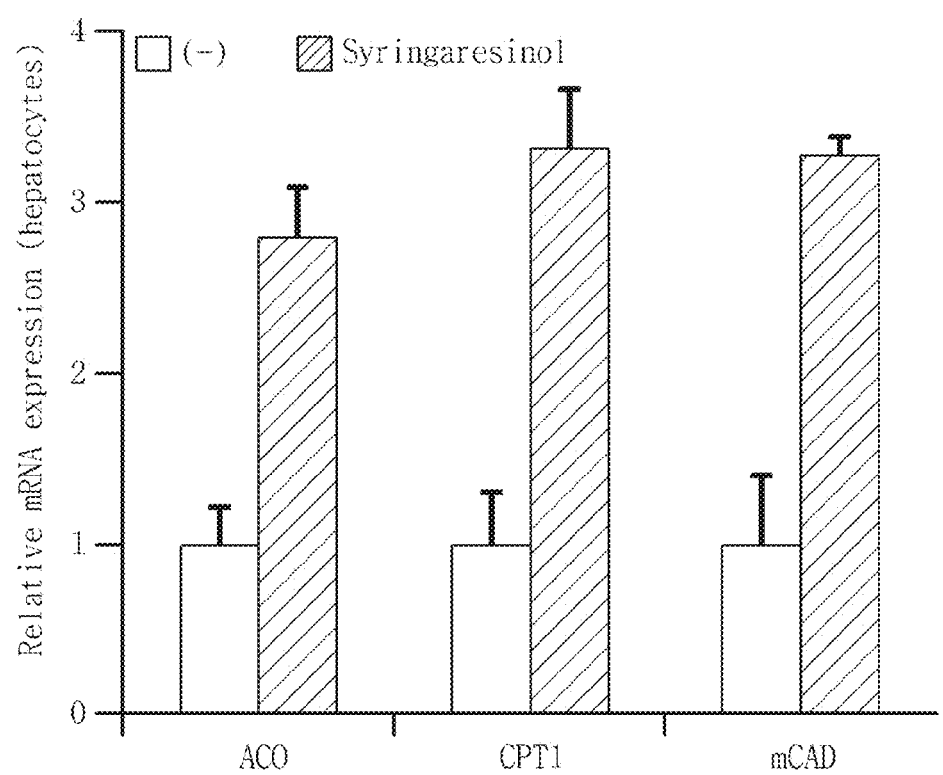
FIG. 9 shows the increase in expression of fatty acid oxidation-related genes in human hepatocytes treated with 50 μM syringaresinol.
Figure 10:
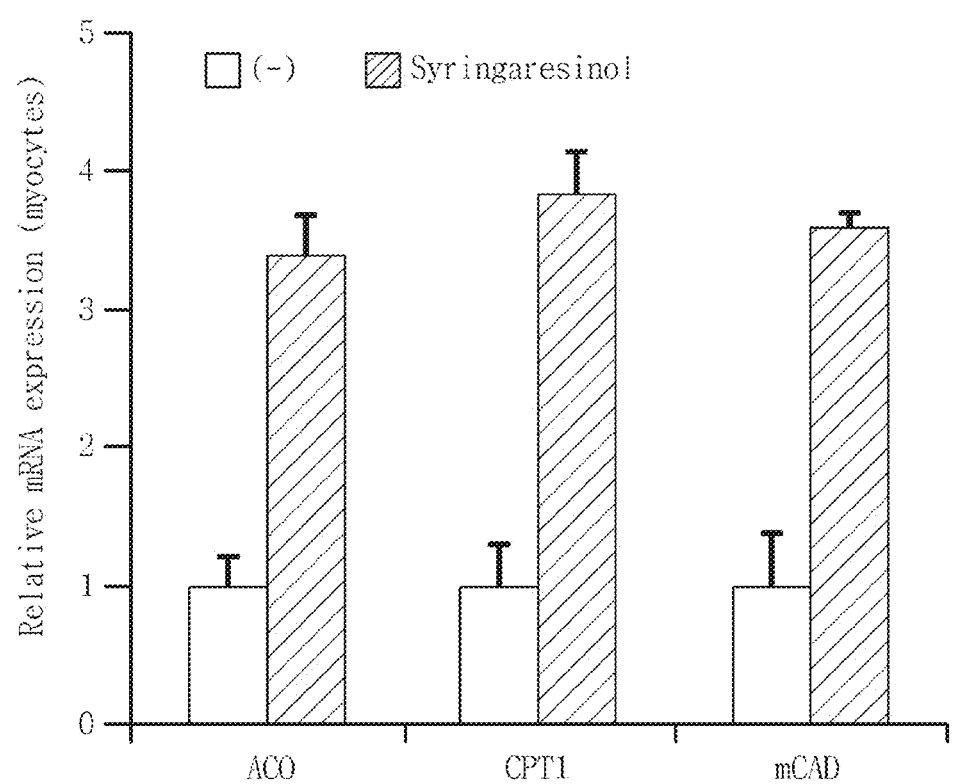
FIG. 10 shows the increase in expression of fatty acid oxidation-related genes in human myocytes treated with 50 μM syringaresinol.

As can be seen from FIGS. 5-7, syringaresinol suppressed the expression of fatty acid synthesis-inducing genes. Also, as can be seen from FIGS. 8-10, syringaresinol increased the expression of fatty acid oxidation promoting genes. Accordingly, it can be seen that syringaresinol can prevent fat accumulation by suppressing fat synthesis and at the same time increasing fat consumption.

[Test Example 5] Evaluation of Fatty Acid Oxidation Promoting Ability

Human adipocytes, hepatocytes and myocytes were treated with 50 μM syringaresinol in substantially the same manner as in Test Example 3. The cells were washed with PBS and cultured for a day in a medium for fatty acid oxidation analysis. The medium was recovered and the amount of $^3H_2O$ was measured. A result of comparing with a non-treated group is shown in FIG. 11.

Figure 11:
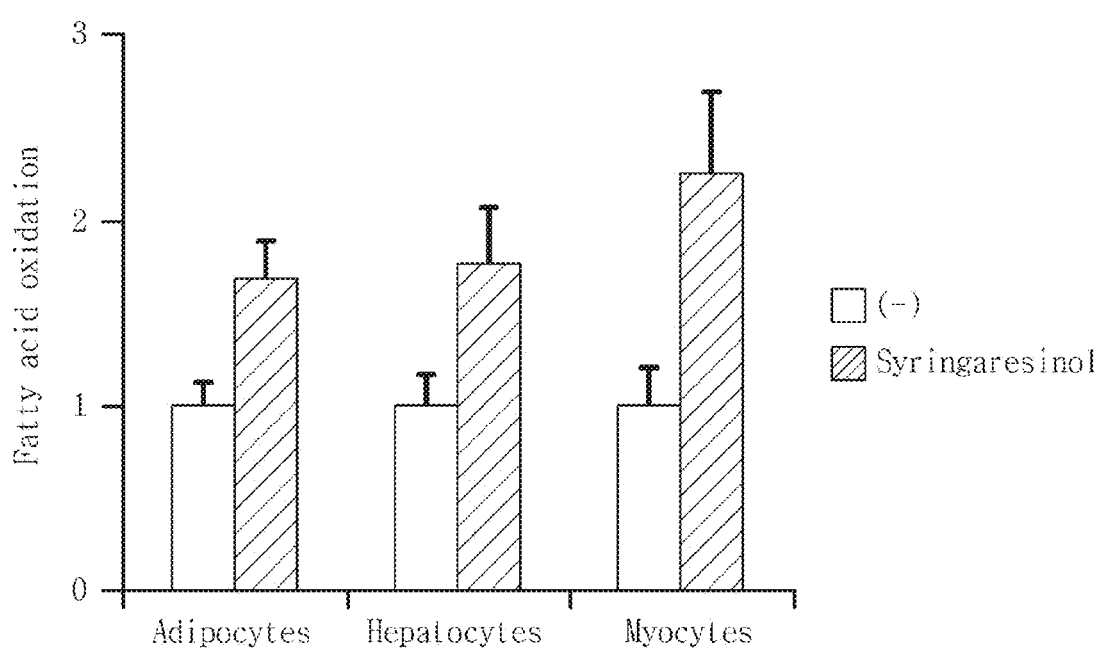
FIG. 11 shows the increase in fatty acid oxidation in human adipocytes, hepatocytes and myocytes treated with 50 μM syringaresinol.

As can be seen from FIG. 11, syringaresinol increased fatty acid oxidation in human adipocytes, hepatocytes and myocytes. Accordingly, it can be seen that syringaresinol can suppress fat accumulation in the body.

[Test Example 6] Evaluation of PGC-1 Expression Promoting Effect of Syringaresinol Human adipocytes, hepatocytes and myocytes were treated with 50 μM syringaresinol in substantially the same manner as in Test Example 3 and washed with PBS. Then, RNA and cDNA were sequentially extracted therefrom. The mRNA expression of the energy metabolism-related genes PGC-1α and PGC-1β was analyzed by qRT-PCR. A result of comparing the expression of PGC-1α and PGC-1β with a control group treated only with DMSO is shown in FIG. 12 and FIG. 13, respectively.

Figure 12:
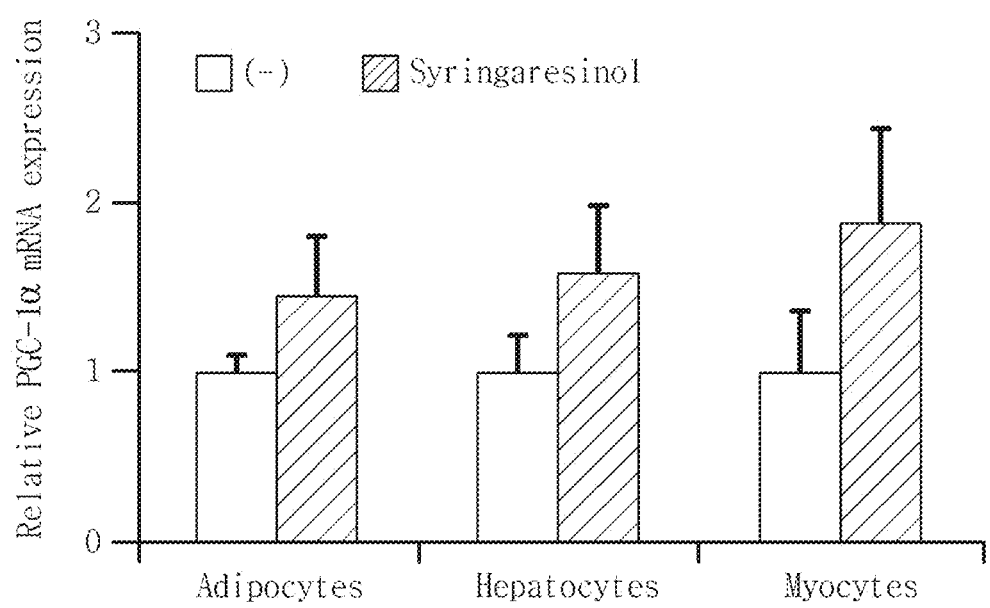
FIG. 12 shows the increase in expression of the energy metabolism regulating gene PGC-1α in human adipocytes, hepatocytes and myocytes treated with 50 μM syringaresinol.
Figure 13:
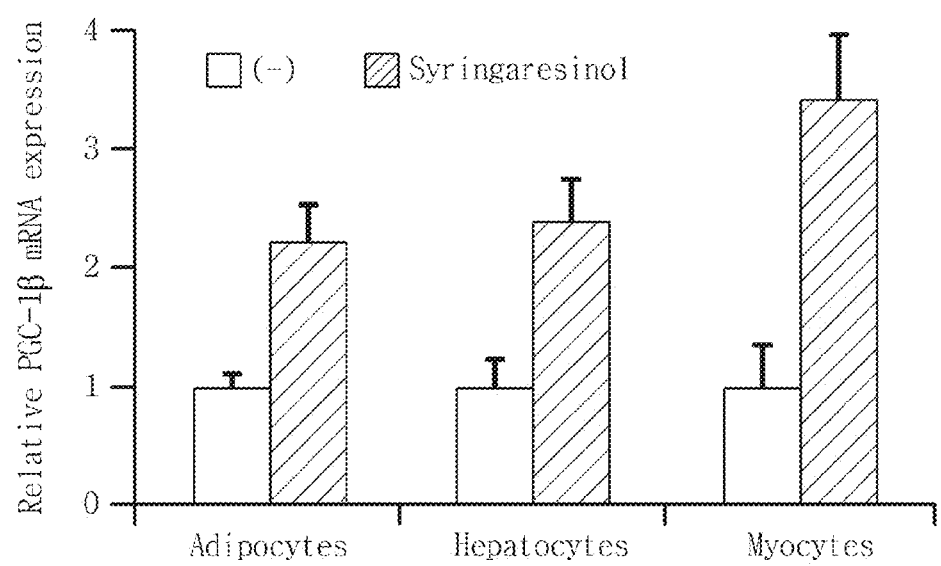
FIG. 13 shows the increase in expression of the energy metabolism regulating gene PGC-1β in human adipocytes, hepatocytes and myocytes treated with 50 μM syringaresinol.

As can be seen from FIG. 12 and FIG. 13, syringaresinol increased the expression of PGC-1α and PGC-1β in human adipocytes, hepatocytes and myocytes. Accordingly, it can be seen that syringaresinol can suppress fat accumulation in the body by facilitating energy metabolism.

[Test Example 7] Evaluation of SIRT1 Expression Promoting Effect in Aged Human Retinal Epithelial Cells The SIRT1 gene expression promoting effect of syringaresinol in aged human retinal epithelial cells was evaluated as follows.

Human retinal endothelial cell line ARPE-19 was purchased from ATCC (Manassa, Va., USA) and cultured in a 5% $CO_2$ incubator using DMEM (Gibco BRL, Grand Island, N.Y., USA) containing 10% bovine serum, 1% penicillin/streptomycin, amphotericin B and an antifungal agent until 70% confluency. The aging of the retinal cells was induced by subculturing until they did not grow any more. The population doubling level (PDL) was calculated according to the following equation for each generation until the cell growth was stopped. The PDL value is higher in aged cells.

$$PDL=(Log_{10}Y-Log_{10}X)/Log_{10}2$$

Y: number of cells at the end of the generation
X: number of cells at the beginning of the generation 5 PDL cells were treated with syringaresinol dissolved in DMSO at a concentration of 50 or 100 μM every other day while inducing aging to 15 PDL cells. The cells of a negative control were treated with DMSO corresponding to 1/1000 of the volume of the culture medium.

The cells treated with each sample were washed 2 times with cold PBS and protein was isolated using the RIPA buffer (Santa Cruz Biotechnology, Santa Cruz, Calif., USA). The isolated protein was quantitated using the BCA assay kit (Pierce, Rockford, USA) and 30 μg was subjected to western blotting using the iBlot Dry blotting system (Invitrogen, Carlsbad, Calif., USA). The SIRT1 protein expression level was measured using anti-SIRT1 antibody (Santa Cruz Biotechnology, Santa Cruz, Calif., USA). The result is shown in FIG. 14.

Figure 14:
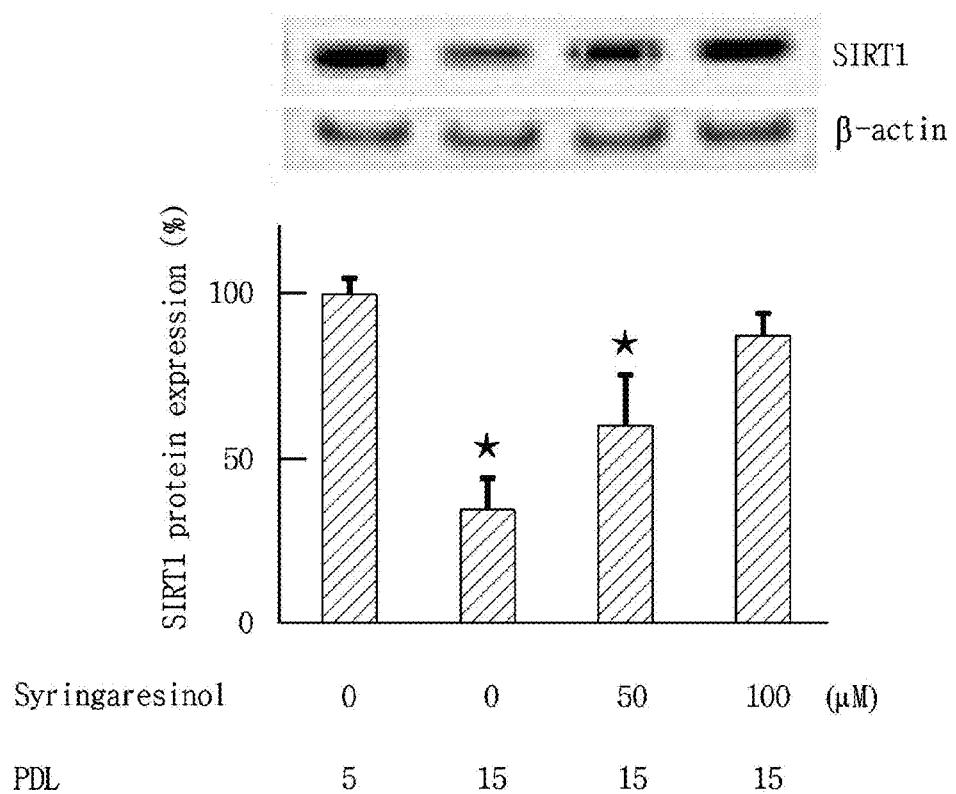
FIG. 14 shows the increase in expression of the SIRT1 gene in aged retinal epithelial cells treated with syringaresinol.

As can be seen from FIG. 14, syringaresinol increased SIRT1 expression, which had been decreased in aged retinal cells, in a concentration-dependent manner. In particular, 100 μM syringaresinol increased SIRT1 expression to a level comparable to that of young retinal epithelial cells. Accordingly, it can be seen that syringaresinol can prevent or improve disease, particularly age-related eye disease, by increasing SIRT1 expression in retinal cells.

[Test Example 8] Evaluation of Mitochondrial Biosynthesis Promoting Effect in Aged Retinal Cells The aging of retinal cells was induced while treating with 50 or 100 μM syringaresinol or with DMSO as a negative control, in substantially the same manner as in Test Example 7. The cells treated with each sample were washed 2 times with cold PBS and genomic DNA (gDNA) was extracted therefrom using the FastPure DNA kit (Tokyo, Japan). For evaluation of mitochondrial biosynthesis, the quantity of the mitochondrial DNA marker cytochrome oxidase subunit II and the nuclear DNA marker cyclophilin A was quantified through real-time PCR using the extracted gDNA and the number of mitochondria was measured by calculating the quantity of mitochondrial DNA relative to the nuclear DNA. PCR reaction and analysis were carried out using the Rotor-Gene 3000 system (Corbett Research, Sydney, Australia). The result is shown in FIG. 15.

Figure 15:
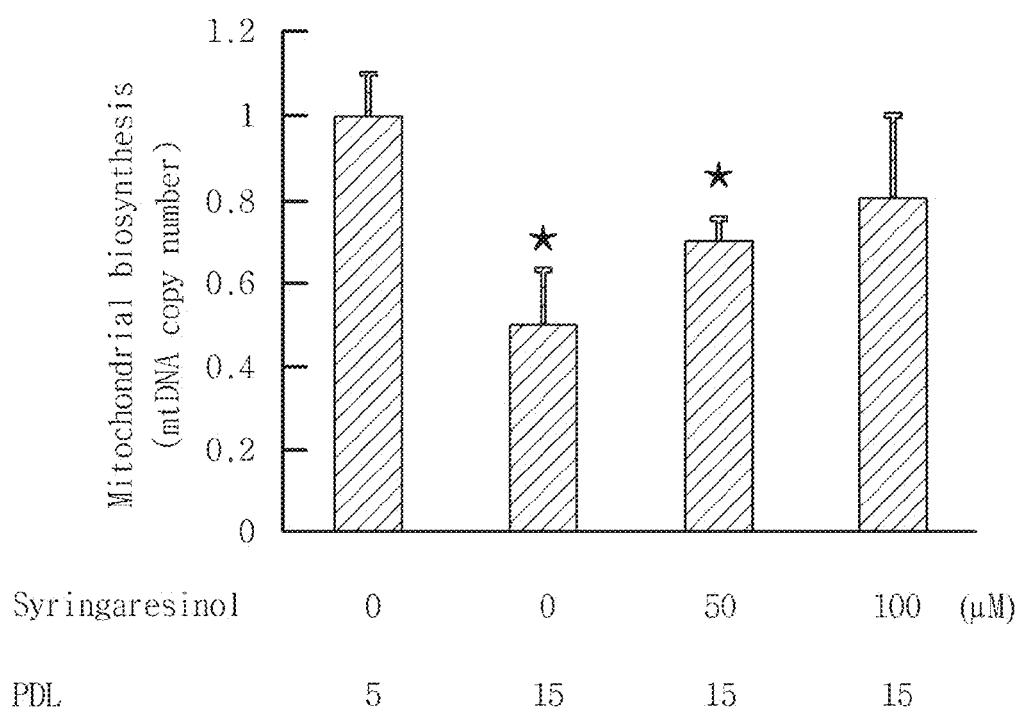
FIG. 15 shows the mitochondrial biosynthesis level in aged retinal epithelial cells treated with syringaresinol.

As can be seen from FIG. 15, the cells treated with 50 and 100 μM syringaresinol exhibited about 40% and 60% increased DMSO. Accordingly, it can be seen that syringaresinol can prevent or improve eye disease by increasing mitochondrial biosynthesis in aged retinal cells in a concentration-dependent manner.

[Test Example 9] Evaluation of Mitochondrial Function Recovering Effect in Aged Retinal Cells The aging of retinal cells was induced while treating with 50 or 100 μM syringaresinol or with DMSO as a negative control, in substantially the same manner as in Test Example 7. For evaluation of mitochondrial function recovering effect, the level of energy (ATP) and reactive oxygen species production in retinal cells was investigated. The energy production was determined by recovering the aged cells after washing with PBS and then with hot water and measuring luminescence using the ATP determination kit (Molecular Probes, Eugene, Oreg., USA) and the Tecan system (Infinite M200, Tecan, Austria). The reactive oxygen species production was measured using a flow cytometer (BD Biosciences, San Jose, Calif., USA) after washing the aged cells with PBS and staining them with the reactive oxygen species detection reagent ($H_2$DCFDA, Invitrogen, Carlsbad, Calif., USA). The result is shown in FIG. 16.

Figure 16:
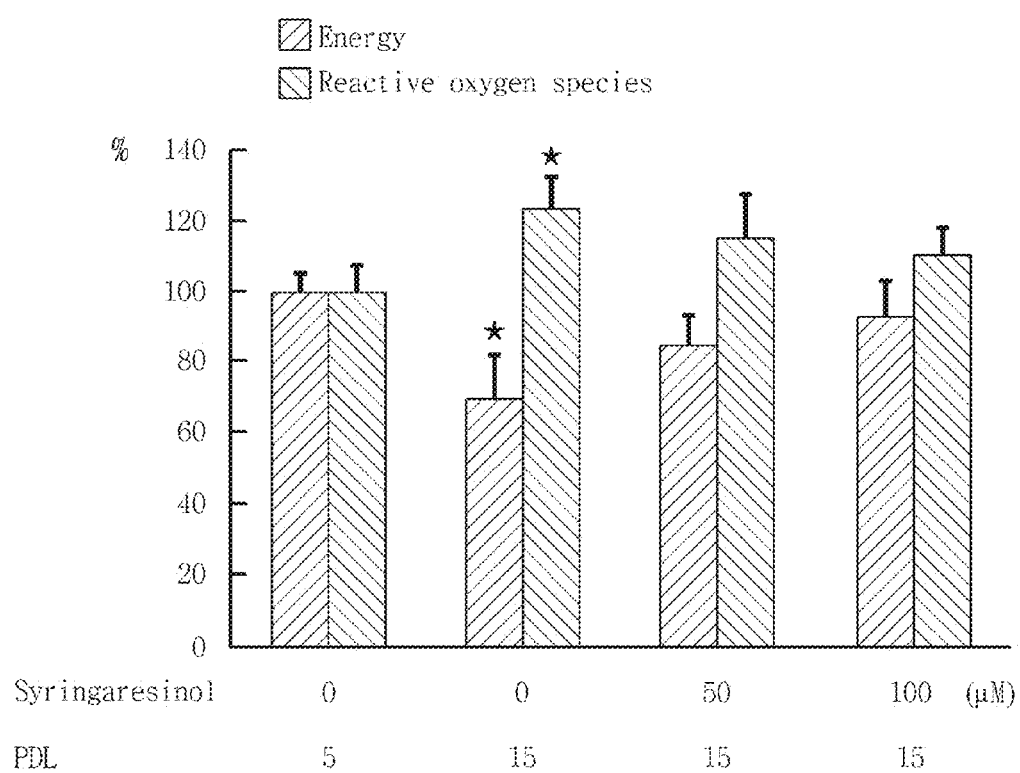
FIG. 16 shows the energy (ATP) and reactive oxygen species production in aged retinal epithelial cells treated with syringaresinol.

As can be seen from FIG. 16, the cells treated with 50 and 100 μM syringaresinol exhibited about 21% and 33% increased energy (ATP) production and about 7% and 11% decreased reactive oxygen species production (significant), as compared to the cells treated only with DMSO. Accordingly, it can be seen that syringaresinol can prevent or improve eye disease by increasing energy production and at the same time decreasing reactive oxygen species production in retinal cells in a concentration-dependent manner.

[Test Example 10] Evaluation of SIRT1 Expression Promoting Effect in Human PBMCs The SIRT1 gene expression promoting effect of syringaresinol in human PBMCs was evaluated as follows.

Human PBMCs were purchased from Zen-Bio (Research Triangle Park, N.C., USA) and cultured in a 5% $CO_2$ incubator using a PBMC medium (Zen-Bio) until 80% confluency. Then, the cells were treated for 24 hours with syringaresinol dissolved in DMSO to a concentration of 20, 50 or 100 μM. A negative control group was treated with DMSO corresponding to 1/1000 of the volume of the culture medium. The cells treated with each sample were washed with PBS and RNA was extracted therefrom using the TRIzol reagent (Invitrogen). Then, cDNA was synthesized from the extracted RNA (5 μg) using a reverse transcription system (Fermentas, Glen Burnie, Md., USA). The expression pattern of the SIRT1 and GAPDH genes was monitored by qRT-PCR using the synthesized cDNA and predesigned primers and probes. qRT-PCR reaction and analysis were carried out using the Rotor-Gene 3000 system (Corbett Research, Sydney, Australia). The result is shown in FIG. 17.

Figure 17:
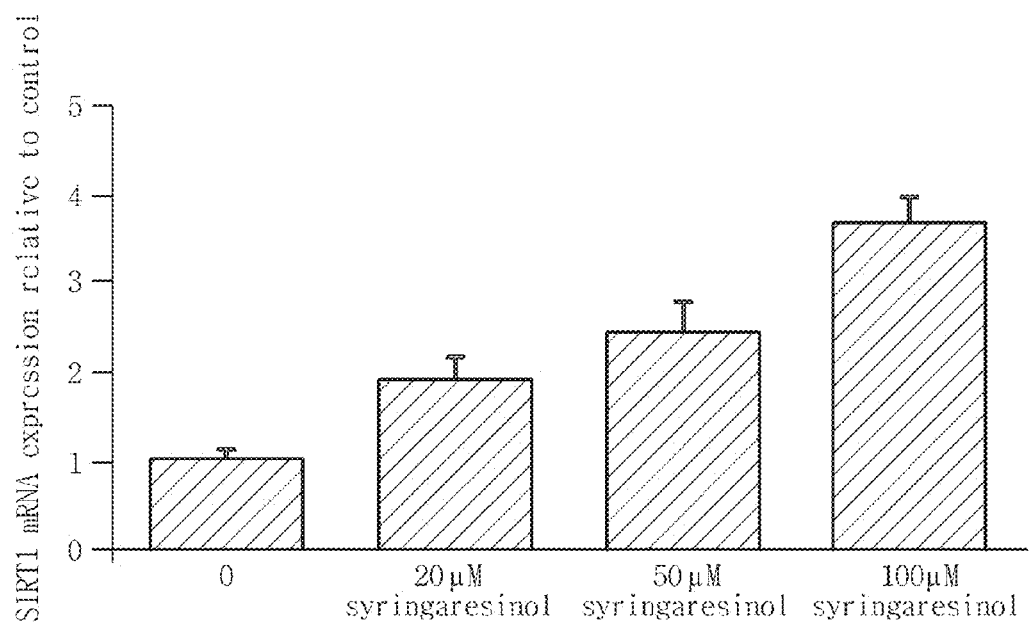
FIG. 17 shows the increase in expression of the SIRT1 gene in human peripheral blood mononuclear cells treated with syringaresinol.

As can be seen from FIG. 17, syringaresinol increased SIRT1 expression in PBMCs in a concentration-dependent manner. Accordingly, it can be seen that syringaresinol can enhance immunity and prevent and improve immune disease by increasing SIRT1 expression in peripheral blood mononuclear cells in a concentration-dependent manner.

[Test Example 11] Evaluation of Reactive Oxygen Species Production Inhibiting Effect in Human PBMCs After pretreating human PBMCs with 20, 50 or 100 μM syringaresinol in substantially the same manner as in Test Example 10, followed by washing with PBS, inflammatory response was induced by treating with 10 ng/mL lipopolysaccharide (LPS). After treating the cells with $H_2$-DCFDA (Invitrogen), which is a fluorescent substance capable of detecting reactive oxygen species, the amount of fluorescent substance was measured using a multiplate reader (Infinite M200; Tecan, Mannedorf, Switzerland). The result is shown in FIG. 18.

Figure 18:
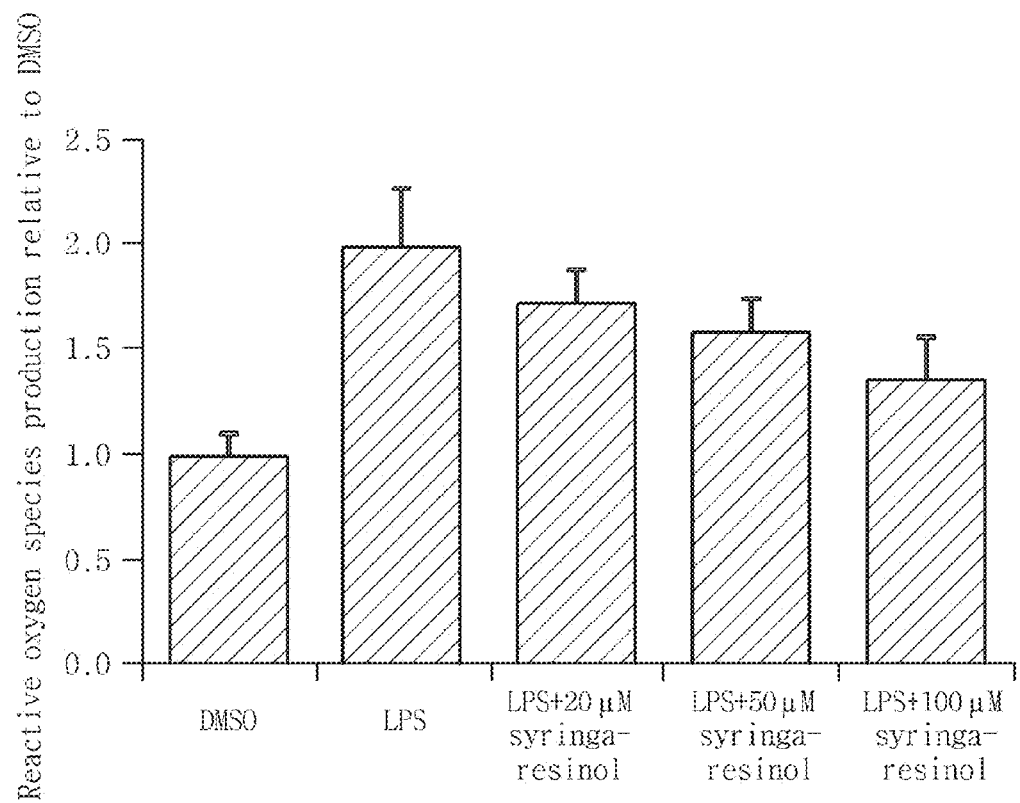
FIG. 18 shows the inhibited reactive oxygen species production in human peripheral blood mononuclear cells treated with syringaresinol.

As can be seen from FIG. 18, the cells treated with syringaresinol exhibited about 60% decreased reactive oxygen species production as compared to the cells treated only with LPS. Accordingly, it can be seen that syringaresinol can enhance immunity and prevent and improve immune disease by reducing reactive oxygen species and thereby suppressing inflammatory response.

[Test Example 12] Evaluation of Effect of Inhibiting Expression of Inflammation-Related Genes in Human PBMCs After pretreating human PBMCs with 50 μM syringaresinol, inflammatory response was induced by treating with 10 ng/mL LPS, in substantially the same manner as in Test Example 11. The cells treated with each sample were washed with PBS and RNA and cDNA were extracted and synthesized therefrom. Then, the expression pattern of the inflammatory response-related genes IL-1b, IL-6, iNOS, COX2, MMP9 and CCR2 was monitored using the synthesized cDNA and predesigned primers. The result is shown in FIG. 19.

Figure 19:
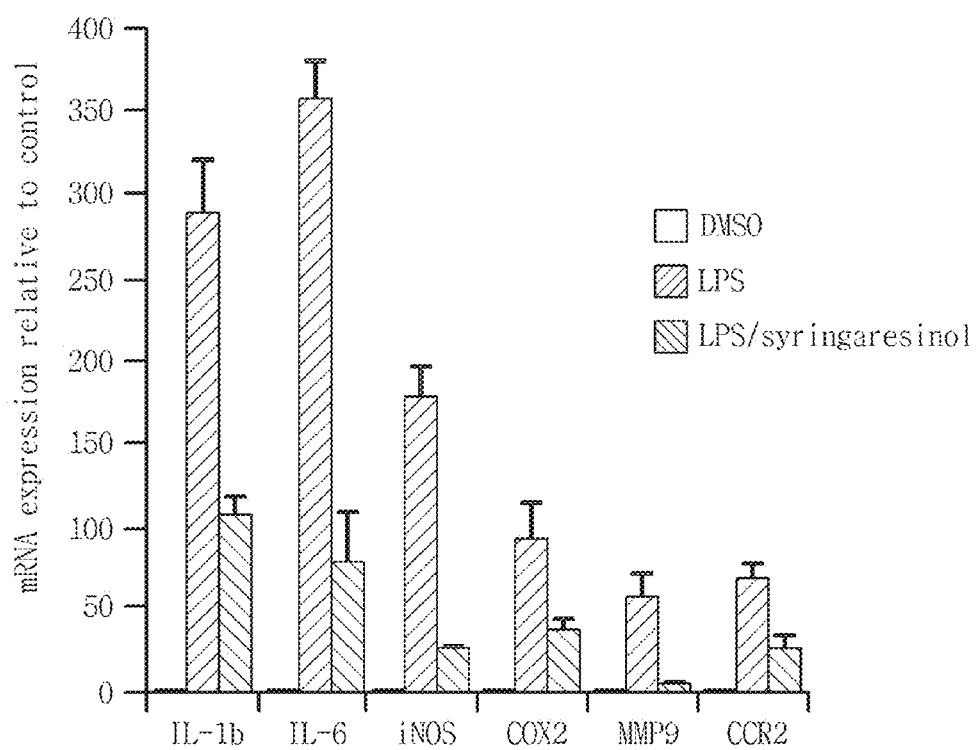
FIG. 19 shows the decrease in expression of inflammatory response-related genes in human peripheral blood mononuclear cells treated with syringaresinol.

As can be seen from FIG. 19, the cells treated with syringaresinol exhibited about 90% decreased expression of the inflammatory response-related genes as compared to the cells treated only with LPS. Accordingly, it can be seen that syringaresinol can enhance immunity and prevent or improve immune disease by reducing inflammatory response.

[Test Example 13] Evaluation of Human PBMC Migration and Deposition Inhibiting Effect After treating human PBMCs with 20, 50 or 100 μM syringaresinol or DMSO in substantially the same manner as in Test Example 11, inflammatory response was induced by treating with 10 ng/mL TNF. After treating differentiated 3T3-L1 adipocytes (Zen-Bio) with the PBMCs, it was investigated whether the PBMCs migrate onto the adipocytes and deposit. 48 hours later, after removing the PBMCs remaining without migrating, the cells were detached from a culture dish using trypsin/EDTA and then counted using a cell counter. The result is shown in FIG. 20.

Figure 20:
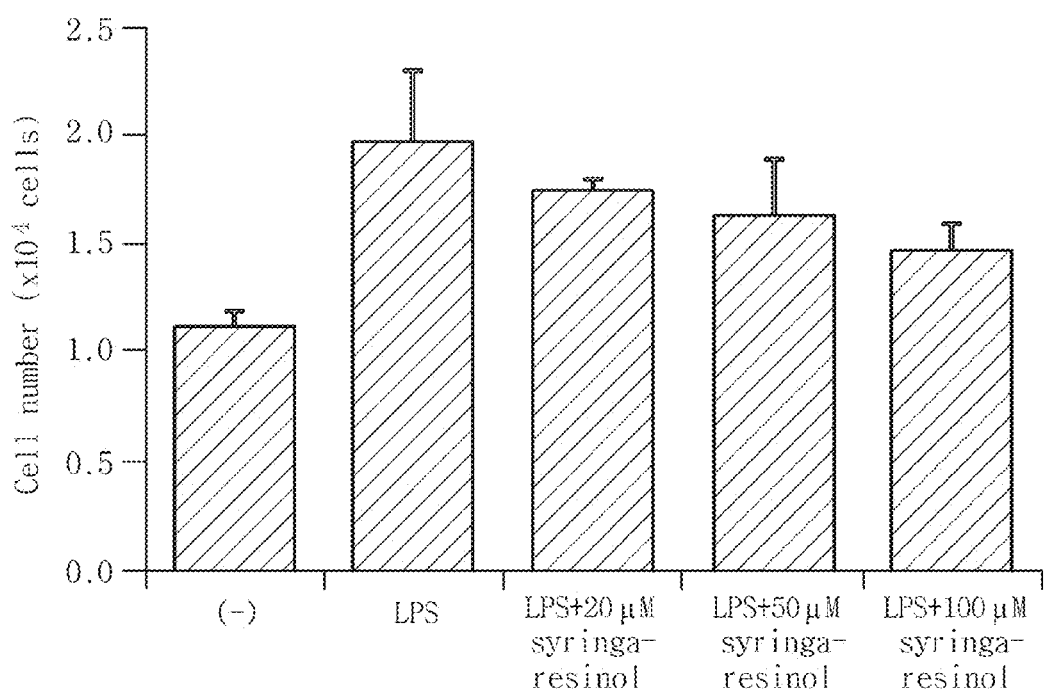
FIG. 20 shows the suppressed migration and tissue deposition of human peripheral blood mononuclear cells treated with syringaresinol.

As can be seen from FIG. 20, syringaresinol inhibited the migration and deposition of the PBMCs onto the adipocytes by about 50%. Since this suggests that syringaresinol can inhibit the migration and deposition of peripheral blood mononuclear cells in response to inflammatory signals, it can be seen that syringaresinol can enhance immunity and prevent or improve immune disease by suppressing inflammatory response.

[Test Example 14] Evaluation of Effect of Inducing Change in Human PBMC Type

After treating human PBMCs with 20, 50 or 100 μM syringaresinol or DMSO in substantially the same manner as in Test Example 11, RNA was extracted from the PBMCs and cDNA was synthesized therefrom in order to measure the expression of type 2 immune cell-related genes. The expression pattern of the transcriptional regulators necessary for inducement of differentiation to type 2 immune cells, such as PGC-1α and PGC-1β, and the genes mainly expressed in type 2 immune cells, such as IL-10 and arginase I, was measured using the synthesized cDNA. The result is shown in FIG. 21.

Figure 21:
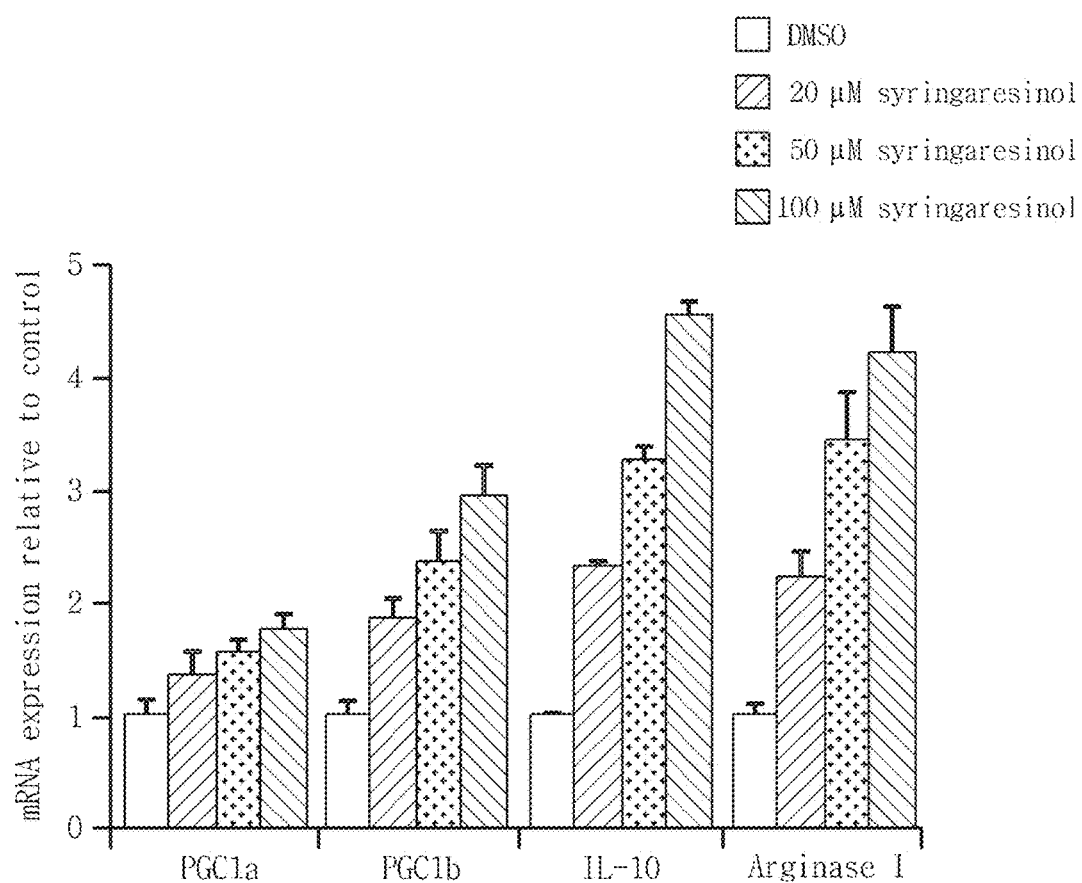
FIG. 21 shows the increase in expression of genes related with conversion to type 2 immune cells in human peripheral blood mononuclear cells treated with syringaresinol.

As can be seen from FIG. 21, the cells treated with syringaresinol exhibited significantly increased expression of type 2 immune cell-specific marker genes. Accordingly, it can be seen that syringaresinol can enhance immunity and prevent or improve immune disease by promoting differentiation of peripheral blood mononuclear cells into type 2 immune cells.

Hereinafter, the present disclosure will be described in detail through formulation examples. However, the formulation examples are for illustrative purposes only and it will be apparent to those of ordinary skill in the art that the scope of the present disclosure is not limited by the formulation examples.

[Formulation Example 1] Health Food

| | |
|---|---|
| Syringaresinol | 1000 mg |
| Vitamin mixture | |
| Vitamin A acetate | 70 μg |
| Vitamin E | 1.0 mg |
| Vitamin B$_1$ | 0.13 mg |
| Vitamin B$_2$ | 0.15 mg |
| Vitamin B$_6$ | 0.5 mg |
| Vitamin B$_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium dihydrogen phosphate | 15 mg |
| Calcium monohydrogen phosphate | 55 mg |
| Potassium citrate | 90 mg |
| Calcium carbonate | 100 mg |
| Magnesium chloride | 24.8 mg |

Although the above-described mixing ratios of the vitamin and mineral mixtures are provided as specific examples suitable for health food, the mixing ratios may be changed as desired.

[Formulation Example 2] Health Drink

| | |
|---|---|
| Syringaresinol | 1000 mg |
| Citric acid | 1000 mg |
| Oligosaccharide | 100 g |
| Taurine | 1 g |
| Purified water | balance |

According to a commonly employed method, the above-described ingredients are mixed and stirred for about 1 hour while heating at about 85° C. The resulting solution is filtered and sterilized.

[Formulation Example 3] Tablet

Granules formed by mixing 100 mg of syringaresinol g, 50 mg of soybean extract, 100 mg of glucose, 50 mg of red ginseng extract, 96 mg of starch and 4 mg of magnesium stearate and adding 40 mg of 30% ethanol are dried at 60° C. and prepared into a tablet.

[Formulation Example 4] Granule

Granules formed by mixing 100 mg of syringaresinol g, 50 mg of soybean extract, 100 mg of glucose and 600 mg of starch and adding 100 mg of 30% ethanol are dried at 60° C. and filled in a pouch.

[Formulation Example 5] Ointment

An ointment is prepared according to a commonly employed method with the composition described in Table 1.

TABLE 1

| Ingredients | Content (wt %) |
|---|---|
| Syringaresinol | 3.0 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Preservative, pigment and fragrance | adequate |
| Purified water | balance |

INDUSTRIAL APPLICABILITY

A composition according to the present disclosure, which contains an SIRT1 activating agent, has superior detoxifying effect, particularly superior effect of detoxifying smoking-induced toxicity.

The composition according to the present disclosure sure, which contains an SIRT1 activating agent, has excellent effect of preventing and improving metabolic disorder, specifically obesity, type 2 diabetes, hyperlipidemia or fatty liver.

The composition according to the present disclosure sure, which contains an SIRT1 activating agent, has excellent effect of preventing or improving eye disease, particularly age-related eye disease.

The composition according to the present disclosure sure, which contains an SIRT1 activating agent, has excellent effect of preventing or improving immune disease such as allergy, atopic dermatitis, hay fever or rheumatoid arthritis.

The invention claimed is:

1. A method for detoxification in a subject suffering from toxicity comprising administering an effective amount of a compound of Chemical Formula 1, or a pharmaceutically acceptable salt thereof to the subject:

[Chemical Formula 1]

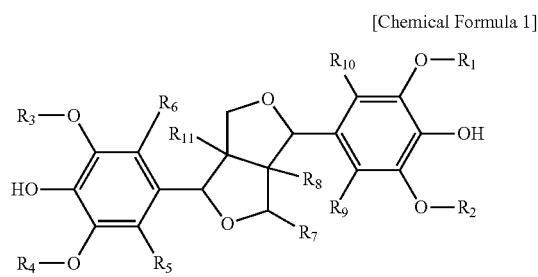

$R_1$, $R_2$, $R_3$ or $R_4$ are independently an unbranched or branched $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group, and $R_5$, $R_6$, $R_7$, $R_8$, $R_9$, $R_{10}$ or $R_{11}$ are independently hydrogen or an unbranched or branched $C_1$-$C_{18}$ alkyl group, $C_1$-$C_{18}$ alkoxy group, $C_1$-$C_{18}$ alkenyl group, $C_1$-$C_{18}$ alkynyl group or $C_3$-$C_6$ cyclic alkyl group, and wherein the detoxification is detoxification to smoking-induced toxicity.

2. The method according to claim 1, wherein the compound is syringaresinol.

3. The method according to claim 2,
wherein the syringaresinol is administered in a form of an agent, and
wherein the agent comprises syringaresinol in an amount of 0.0001-10 wt % based on the total weight of the agent.

4. The method according to claim 2, wherein the syringaresinol is included in an extract of one or more selected from flax seed, phellodendri cortex, acanthopanacis cortex, sesame seed and ginseng berry.

5. The method according to claim 3, wherein the agent is administered in a form of a composition, and
the composition comprises 0.001-20 wt % of the SIRT1 activating agent based on the total weight of the composition.

6. The method according to claim 5, wherein the composition is a food composition.

7. The method according to claim 5, wherein the composition is a pharmaceutical composition.

* * * * *